US011272905B2

(12) United States Patent
Kurita et al.

(10) Patent No.: US 11,272,905 B2
(45) Date of Patent: Mar. 15, 2022

(54) MEDICAL IMAGE DIAGNOSTIC APPARATUS AND MEDICAL IMAGE PROCESSING APPARATUS

(71) Applicant: TOSHIBA MEDICAL SYSTEMS CORPORATION, Otawara (JP)

(72) Inventors: Koichiro Kurita, Nasushiobara (JP); Masaki Watanabe, Shioya (JP); Eiji Goto, Utsunomiya (JP); Shogo Fukuda, Otawara (JP)

(73) Assignee: Canon Medical Systems Corporation, Otawara (JP)

( * ) Notice: Subject to any disclaimer, the term of this patent is extended or adjusted under 35 U.S.C. 154(b) by 671 days.

(21) Appl. No.: 14/802,259

(22) Filed: Jul. 17, 2015

(65) Prior Publication Data

US 2016/0015364 A1     Jan. 21, 2016

(30) Foreign Application Priority Data

Jul. 18, 2014    (JP) .............................. JP2014-148175

(51) Int. Cl.
     *A61B 8/08*        (2006.01)
     *A61B 8/14*        (2006.01)
     (Continued)

(52) U.S. Cl.
     CPC .............. *A61B 8/468* (2013.01); *A61B 5/055* (2013.01); *A61B 5/4362* (2013.01); *A61B 6/468* (2013.01);
     (Continued)

(58) Field of Classification Search
     CPC ........ A61B 8/468; A61B 8/0866; A61B 6/468
     See application file for complete search history.

(56) References Cited

U.S. PATENT DOCUMENTS 5,605,155 A * 2/1997 Chalana ............... A61B 5/1075
                                                            600/443
5,795,296 A * 8/1998 Pathak ................. A61B 5/1075
                                                            600/443

(Continued)

FOREIGN PATENT DOCUMENTS

CN      101069647 A     11/2007
CN      101779969 A     7/2010
(Continued)

OTHER PUBLICATIONS

English language translation provided by EPO/Google of JP 2009-261800 A.*

(Continued)

*Primary Examiner* — Colin T. Sakamoto
(74) *Attorney, Agent, or Firm* — Oblon, McClelland, Maier & Neustadt, L.L.P.

(57) ABSTRACT

A medical image diagnostic apparatus according to the embodiment includes a scanner, image generating circuitry, marker generating circuitry, and control circuitry. The scanner performs scanning to generate an image of the inside of a subject. The image generating circuitry generates an image based on the result of scanning performed by the scanner. The marker generating circuitry generates a marker provided with information at a position serving as a reference for comparison with a certain structure. The control circuitry displays the image and the marker on the same screen of a display.

19 Claims, 18 Drawing Sheets

(51) Int. Cl.
  *A61B 5/055* (2006.01)
  *A61B 8/00* (2006.01)
  *A61B 6/00* (2006.01)
  *A61B 5/00* (2006.01)
  *A61B 6/03* (2006.01)
(52) U.S. Cl.
  CPC ............ *A61B 8/0866* (2013.01); *A61B 8/463* (2013.01); *A61B 6/032* (2013.01); *A61B 8/085* (2013.01); *A61B 8/14* (2013.01); *A61B 2503/02* (2013.01)

(56) References Cited

U.S. PATENT DOCUMENTS

| | | | | |
|---|---|---|---|---|
| 5,838,592 | A * | 11/1998 | Spratt | A61B 8/0866 |
| | | | | 702/155 |
| 6,019,723 | A * | 2/2000 | Yamaura | A61B 5/1075 |
| | | | | 600/437 |
| 2006/0135855 | A1* | 6/2006 | Alsafadi | G16H 10/60 |
| | | | | 600/300 |
| 2007/0287915 | A1 | 12/2007 | Akaki et al. | |
| 2010/0185094 | A1 | 7/2010 | Hamada et al. | |
| 2012/0130223 | A1* | 5/2012 | Reicher | G06F 19/321 |
| | | | | 600/407 |
| 2012/0179039 | A1* | 7/2012 | Pelissier | A61B 8/4263 |
| | | | | 600/443 |
| 2013/0116548 | A1* | 5/2013 | Kumar | A61B 8/0841 |
| | | | | 600/424 |
| 2013/0201210 | A1* | 8/2013 | Vaddadi | G06T 19/006 |
| | | | | 345/632 |
| 2013/0208970 | A1 | 8/2013 | Fujisawa | |
| 2014/0276057 | A1* | 9/2014 | Lee | A61B 8/462 |
| | | | | 600/441 |
| 2014/0378828 | A1* | 12/2014 | Penenberg | A61F 2/4657 |
| | | | | 600/424 |
| 2015/0257738 | A1* | 9/2015 | Kim | A61B 8/463 |
| | | | | 600/440 |
| 2015/0265247 | A1* | 9/2015 | Roh | A61B 8/465 |
| | | | | 600/438 |
| 2016/0310761 | A1* | 10/2016 | Li | A61N 5/1038 |
| 2017/0090675 | A1* | 3/2017 | Lee | A61B 8/468 |

FOREIGN PATENT DOCUMENTS

| | | | |
|---|---|---|---|
| CN | 103228216 A | 7/2013 | |
| DE | 3737582 A1 * | 5/1989 | ........... A61B 5/1072 |
| JP | S56-073032 | 6/1981 | |
| JP | 4-54628 | 2/1992 | |
| JP | 11-113901 | 1/1999 | |
| JP | 2003-123086 | 4/2003 | |
| JP | 2009-261800 | 11/2009 | |

OTHER PUBLICATIONS

Combined Chinese Office Action and Search Report dated Aug. 1, 2017 in Patent Application No. 201510408645.3 (with English Translation of Category of Cited Documents).

Office Action dated May 28, 2019, in corresponding Japanese Patent Application No. 2015-111747, 17 pages.

Japanese Office Action dated Feb. 12, 2019 in Japanese Application No. 2015-111747, 4 pages.

* cited by examiner

FIG.3

51
EXAMINATION REGISTRATION SCREEN

Exam Type [OB ▼]  511

ID [        ]   Date of Birth [  ] / [  ] / [  ]  512

Last Name [        ]

First Name [        ]

MI [        ]

[PREV ▼] [AUG. 19, 2013]  GA [20] w [  ] d  513

FIG.4

52
SCALE CONDITION SETTING SCREEN

| MEASUREMENT ITEM 1 | FL ▼ | MARKER DATA | XYZ ▼ | TYPE | STRAIGHT LINE ▼ | |
|---|---|---|---|---|---|---|
| UNIT | WEEK ▼ | DISPLAY POSITION | 70% | BEFORE 1 WEEK ▼ | AFTER 1 WEEK ▼ | 521 |
| DATE OF PREVIOUS EXAMINATION | DISPLAY ▼ | | NORMAL RANGE DISPLAY | DISPLAY ▼ | | |

| MEASUREMENT ITEM 2 | AC ▼ | MARKER DATA | XYZ ▼ | TYPE | CIRCLE ▼ | |
|---|---|---|---|---|---|---|
| UNIT | WEEK ▼ | DISPLAY POSITION | 70% | BEFORE 1 WEEK ▼ | AFTER 1 WEEK ▼ | 522 |
| DATE OF PREVIOUS EXAMINATION | NOT DISPLAY ▼ | | NORMAL RANGE DISPLAY | NOT DISPLAY ▼ | | |

| MEASUREMENT ITEM 3 | BPD ▼ | MARKER DATA | XYZ ▼ | TYPE | STRAIGHT LINE ▼ | |
|---|---|---|---|---|---|---|
| UNIT | WEEK ▼ | DISPLAY POSITION | 70% | BEFORE 1 WEEK ▼ | AFTER 1 WEEK ▼ | 523 |
| DATE OF PREVIOUS EXAMINATION | NOT DISPLAY ▼ | | NORMAL RANGE DISPLAY | NOT DISPLAY ▼ | | |

| MEASUREMENT ITEM 4 | ▼ | TYPE | ▼ | BEFORE | ▼ | AFTER | ▼ |
|---|---|---|---|---|---|---|---|
| DISPLAY POSITION | ▼ | | | DATE OF PREVIOUS EXAMINATION | | ▼ | 524 |
| NORMAL RANGE DISPLAY | ▼ | | STATISTICAL DATA | | ▼ | | |

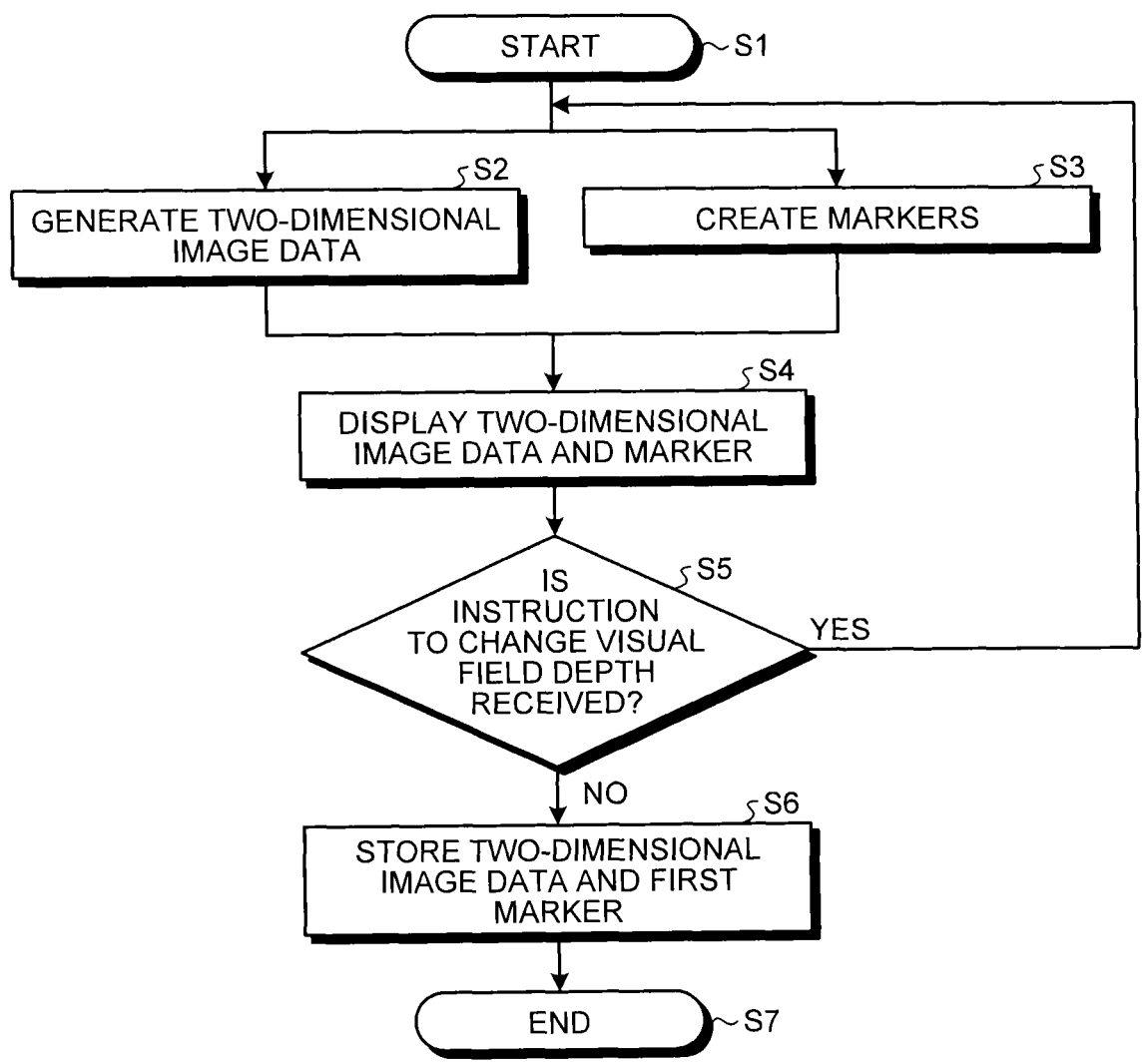

31
FIRST MARKER

32
SECOND MARKER

MEDICAL IMAGE DIAGNOSTIC APPARATUS AND MEDICAL IMAGE PROCESSING APPARATUS

CROSS-REFERENCE TO RELATED APPLICATIONS

This application is based upon and claims the benefit of priority of the prior Japanese Patent Application No. 2014-148175, filed on Jul. 18, 2014, the entire contents of which are incorporated herein by reference. The entire contents of the prior Japanese Patent Application No. 2015-111747, filed on Jun. 1, 2015, are also incorporated herein by reference.

FIELD

Embodiments described herein relate generally to a medical image diagnostic apparatus and a medical image processing apparatus.

BACKGROUND

Ultrasonic diagnostic apparatuses transmit ultrasonic waves to the inside of a subject and receive ultrasonic waves reflected by a difference in the acoustic impedance of a subject tissue with a simple operation of bringing an ultrasonic probe into contact with the body surface of the subject. Ultrasonic diagnostic apparatuses can generate image data based on the received ultrasonic waves and display the generated image data on a monitor in real time. Thus, ultrasonic diagnostic apparatuses are widely used for examinations of hearts, blood vessels, abdomens, and urinary organs in living bodies, and examinations performed in departments of obstetrics and gynecology.

Ultrasonic diagnostic apparatuses can also measure and analyze a diagnosed site of the subject from the generated image data using application software. To make a measurement, an operator performs, when the monitor displays image data of the diagnosed site, an operation for stopping the image data. If the stopped image data is not a desired one, the operator performs an operation for selecting image data from pieces of stored image data by going back to a predetermined time before the stop operation is performed. Subsequently, the operator selects a measurement item and performs an operation for specifying a measurement position, for example. In a case where the examination target is a fetus, the operator also performs an operation for selecting a diagnostic item, such as an estimated weight. The operator needs to perform the series of operations during the examination.

Because the operator needs to perform the series of operations during the examination, work in the examination is made complicated.

BRIEF DESCRIPTION OF THE DRAWINGS

FIG. 3 is a view of an example of an examination registration screen displayed on a display according to the first embodiment;

FIG. 4 is a view of an example of a marker condition setting screen displayed on the display according to the first embodiment;

FIG. 5 is a flowchart of an operation of the ultrasonic diagnostic apparatus according to the first embodiment;

DETAILED DESCRIPTION

A medical image diagnostic apparatus according to the embodiment includes a scanner, image generating circuitry, marker generating circuitry, and control circuitry. The scanner performs scanning to generate an image of the inside of a subject. The image generating circuitry generates an image based on the result of scanning performed by the scanner. The marker generating circuitry generates a marker provided with information at a position serving as a reference for comparison with a certain structure. The control circuitry displays the image and the marker on the same screen of a display.

Exemplary embodiments of a medical image diagnostic apparatus and a medical image processing apparatus are described below with reference to the accompanying drawings. Embodiments are not limited to the embodiments below. The contents described in one embodiment are basically applicable to the other embodiments.

First Embodiment

Figure 1:
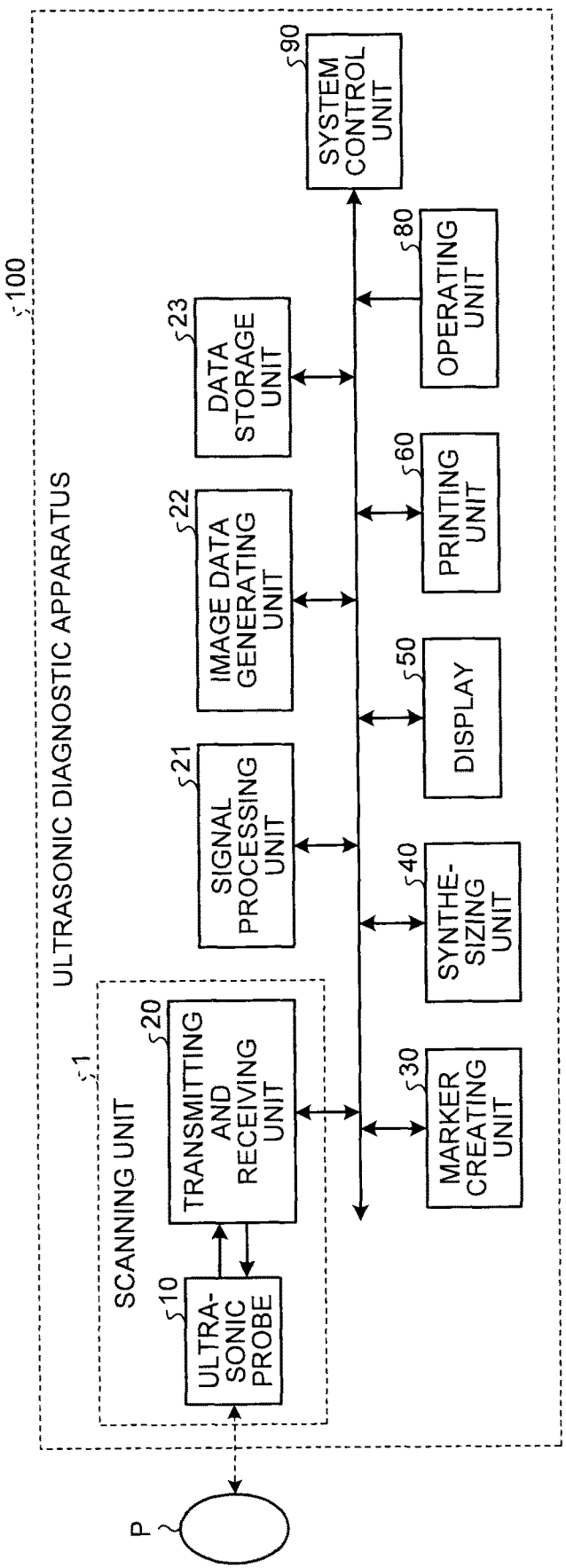
FIG. 1 is a block diagram of a configuration of an ultrasonic diagnostic apparatus according to a first embodiment.

A first embodiment describes an ultrasonic diagnostic apparatus as an example of the medical image diagnostic apparatus. FIG. 1 is a block diagram of a configuration of an ultrasonic diagnostic apparatus according to the first embodiment. An ultrasonic diagnostic apparatus 100 includes a scanning unit 1 (also called scanner). The scanning unit 1 performs scanning to generate an image of the inside of a subject P. For example, the scanning unit 1 includes an ultrasonic probe 10 and a transmitting and receiving unit 20. The ultrasonic probe 10 performs ultrasonic scanning on a subject P. The transmitting and receiving unit 20 causes the ultrasonic probe 10 to perform ultrasonic scanning and processes received signals obtained by the ultrasonic scanning performed by the ultrasonic probe 10. The ultrasonic diagnostic apparatus 100 further includes a signal processing unit 21 and an image data generating unit 22. The signal processing unit 21 generates data from the signals processed by the transmitting and receiving unit 20. The image data generating unit 22 generates image data based on the data generated by the signal processing unit 21.

The ultrasonic diagnostic apparatus 100 further includes a data storage unit 23 and a marker creating unit 30. The data storage unit 23 stores therein the image data generated by the image data generating unit 22, for example. The marker creating unit 30 creates a scale-like marker used for comparison with the size of a region of interest on the image data generated by the image data generating unit 22 or measurement of the size of the region of interest. The ultrasonic diagnostic apparatus 100 further includes a synthesizing unit 40 that synthesizes the image data generated by the image data generating unit 22 and the marker created by the marker creating unit 30.

The ultrasonic diagnostic apparatus 100 further includes a display 50, a printing unit 60, and an operating unit 80. The display 50 outputs to display the image data and the marker synthesized by the synthesizing unit 40. The printing unit 60 outputs to print the image data and the marker. The operating unit 80 inputs command signals and the like. The ultrasonic diagnostic apparatus 100 further includes a system control unit 90 that controls the transmitting and receiving unit 20, the signal processing unit 21, the image data generating unit 22, the data storage unit 23, the marker creating unit 30, the synthesizing unit 40, the display 50, and the printing unit 60.

The ultrasonic probe 10 includes a plurality of two-dimensionally arrayed transducer elements that perform ultrasonic scanning on the subject P, for example. The ultrasonic probe 10 transmits ultrasonic waves to the inside of the subject P based on drive signals received from the transmitting and receiving unit 20. The ultrasonic probe 10 receives ultrasonic waves reflected in the subject P and converts them into received signals.

The transmitting and receiving unit 20 includes a transmitting unit and a receiving unit. The transmitting unit generates the drive signals that drive the transducer elements of the ultrasonic probe 10. The receiving unit performs phasing addition on the received signals obtained from the transducer elements of the ultrasonic probe 10. The transmitting and receiving unit 20 causes the ultrasonic probe 10 to perform two-dimensional or three-dimensional ultrasonic scanning based on imaging conditions, such as a gain, a dynamic range, a transmission frequency, a pulse repetition frequency, a visual field depth, a viewing angle, and a frame rate, supplied from the system control unit 90 by an input from the operating unit 80.

After the transducer elements of the ultrasonic probe 10 are driven to perform ultrasonic scanning on the subject P, the signal processing unit 21 processes the received signals subjected to phasing addition by the transmitting and receiving unit 20. Thus, the signal processing unit 21 generates received data on one scanning line, for example. The signal processing unit 21 generates received data (two-dimensional data) corresponding to a two-dimensional area of the subject or received data (three-dimensional data) corresponding to a three-dimensional area of the subject based on a plurality of pieces of received data corresponding to a plurality of respective scanning lines.

Figure 2:
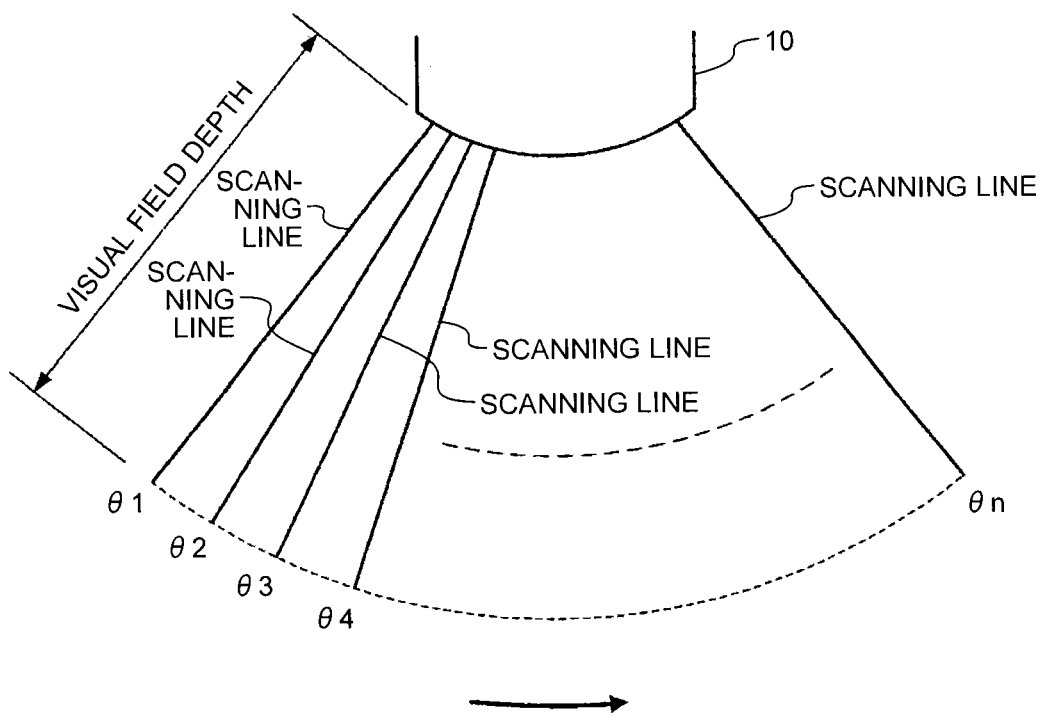
FIG. 2 is a schematic of an example of ultrasonic scanning performed by an ultrasonic probe according to the first embodiment.

The image data generating unit 22 generates an image based on a result of scanning performed by the scanning unit 1. For example, the image data generating unit 22 carries out allocation for coordinate conversion on the two-dimensional data generated by the signal processing unit 21, thereby generating two-dimensional image data or three-dimensional image data. The image data generating unit 22, for example, generates two-dimensional image data corresponding to a scanning range defined by a visual field depth and transmission and reception directions θ1 to θn illustrated in FIG. 2. The two-dimensional image data is composed of pixels having luminance corresponding to the intensity of reflected ultrasonic waves in the visual field depth and the scanning range. The image data generating unit 22 generates multi-planar reconstruction (MPR) image data as two-dimensional image data indicating a certain section in the three-dimensional image data.

The data storage unit 23 stores therein the two-dimensional image data, the three-dimensional image data, and the MPR image data generated by the image data generating unit 22. The data storage unit 23 also stores therein the image data and the marker synthesized by the synthesizing unit 40. The data storage unit 23 also stores therein marker data used to create a marker by the marker creating unit 30 for each author.

The marker data corresponds to a standard value indicated by the average of the femur length, the abdominal circumference, and the biparietal diameter, for example, or a normal range indicated by a 95% confidence interval including the standard value with a probability of 95%. The standard value is statistically calculated from a number of pieces of clinical data obtained by measuring fetuses at each age indicated by the number of weeks or days of pregnancy as information on the pregnancy period.

The marker creating unit 30 generates a marker provided with information at a position serving as a reference for comparison with the certain structure. The information includes at least one of a scale mark, numerical information, and characteristic information. The information includes numerical information indicating at least one of number of months of pregnancy, number of weeks of pregnancy, and number of days of pregnancy. The marker has the information provided in plurality. For example, the marker creating unit 30 creates a marker based on the visual field depth included in the imaging conditions received from the operating unit 80 and on the marker data stored in the data storage unit 23. The marker includes information on the pregnancy period used for comparison with the size of the region of interest on the image data generated by the image data generating unit 22 or measurement of the size of the region of interest. In other words, the marker has the information at a position assumed to correspond to a size of the certain structure at time of scanning performed by the scanning unit 1. The marker creating unit 30 calculates the length (number of pixels) on the image data corresponding to the actual length based on the visual field depth. The marker creating unit 30 then creates a marker of a scale corresponding to the actual length of the region of interest on the image data based on the calculated length. The marker may be represented by a square. The marker may be represented by a simple closed curve. The synthesizing unit 40 synthesizes the image data generated by the image data generating unit 22 and the marker created by the marker creating unit 30.

The display 50 includes a liquid-crystal panel, for example, and displays in real time the image data generated by the image data generating unit 22. The display 50 displays in real time the image data and the marker synthesized by the synthesizing unit 40. The display 50 also displays a marker condition setting screen used to set the conditions of the marker to be created by the marker creating unit 30. The display 50 also displays an examination registration screen used to set examination information on the subject P to be examined.

The operating unit 80 includes an input device, such as a trackball and a switch. The operating unit 80 is used for an input of the imaging conditions, such as a gain, a dynamic range, a transmission frequency, a pulse repetition frequency, a visual field depth, a viewing angle, and a frame rate, an input for setting the marker conditions, an input for setting the examination information, and an input for starting and ending an examination, for example.

The system control unit 90 includes a central processing unit (CPU) and a storage circuit. The system control unit 90 collectively controls the transmitting and receiving unit 20, the signal processing unit 21, the image data generating unit 22, the marker creating unit 30, the synthesizing unit 40, the display 50, and the printing unit 60 based on the input information received from the operating unit 80. For example, the system control unit 90 displays the image and the marker on the same screen of the display 50.

The following describes an example of an operation of the ultrasonic diagnostic apparatus 100 with reference to FIGS. 1 to 13.

When the operating unit 80 inputs an instruction for displaying the examination registration screen to perform an obstetric examination on the subject P of a pregnant woman, the display 50 displays the examination registration screen. An input from the operating unit 80 sets the examination information on the screen.

FIG. 3 is a view of an example of the examination registration screen displayed on the display 50. An examination registration screen 51 includes a first column 511, a second column 512, and a third column 513, for example. The first column 511 is used to set the type of the examination. The second column 512 is used to set identification information for identifying the subject P. The third column 513 is displayed based on the setting in the first column 511.

In a case where the subject P is a pregnant woman, the first column 511 displays "OB (obstetrics)" set by selecting and inputting the department of obstetrics from a plurality of examination departments. In the second column 512, the identification information is input and set, including an ID for identifying the subject P to be examined, the name, and the date of birth, for example.

In the third column 513, any one of "estimated date of delivery (EDD)", "clinical date (CLIN)", "last menstrual period (LMP)", "previous date (PREV)", and "in-vitro fertilization date (IVF)" is selected and input to set the number of weeks of pregnancy on the day of the examination of the subject P, for example. Alternatively, the selection may be made to set the number of days of pregnancy.

In a case where "EDD" is selected, the number of weeks of pregnancy on the day of the examination is calculated and set by inputting the estimated date of delivery. In a case where "CLIN" is selected, the number of weeks of pregnancy on the day of the examination is input and set. In a case where "LMP" is selected, the number of weeks of pregnancy on the day of the examination is calculated and set by inputting the date of the last menstrual period. In a case where "PREV" is selected, the number of weeks of pregnancy on the day of the examination is calculated and set by inputting the date of the previous examination and the number of weeks of pregnancy at the date. In a case where "IVF" is selected, the number of weeks of pregnancy on the day of the examination is calculated and set by inputting the in-vitro fertilization date.

In this example, the third column 513 displays "PREV" that is selected and input. The third column 513 also displays "Aug. 19, 2013" input and displayed as the date of the previous examination, for example. The third column 513 also displays "20" indicating that 20 represents the number of weeks of pregnancy on the day of the examination calculated based on an input of the number of weeks of pregnancy at the date of the previous examination.

After the setting of the examination information on the subject P, when the operating unit 80 inputs an instruction for displaying the marker condition setting screen to set the conditions of the marker to be created by the marker creating unit 30, the display 50 displays the marker condition setting screen.

FIG. 4 is a view of an example of the marker condition setting screen displayed on the display 50. A marker condition setting screen 52 includes a first measurement column 521 to a fourth measurement column 524 in which the marker conditions can be set, for example.

In the first measurement column 521, first marker conditions are set to create a first marker used for the first measurement. The first measurement column 521 displays "femur length (FL)" selected and input to set the femur length from a plurality of measurement items as a site to be measured first. The first measurement column 521 also displays "XYZ" selected and input to set a certain author from a plurality of authors stored in the data storage unit 23 as marker data used to create the marker. The first measurement column 521 also displays "straight line" selected and input to set a shape corresponding to the set measurement item as the shape of the marker.

The first measurement column 521 also displays "week" selected and input to set the number of weeks from the number of weeks and the number of days as the unit of measurement. The first measurement column 521 also displays "70%" input to set the position of the number of weeks of pregnancy on the day of the examination. The first measurement column 521 also displays "1" selected and input to set the number of weeks of pregnancy of a week ago as the number of weeks of pregnancy before the day of the examination.

The first measurement column 521 also displays "1" selected and input to set the number of weeks of pregnancy of a week later as the number of weeks of pregnancy after the day of the examination. The first measurement column 521 also displays "display" selected and input to display the position at which the measurement was made on the day of the previous examination. The first measurement column 521 also displays "display" selected and input to display the normal range for the number of weeks of pregnancy on the day of the examination.

In second measurement column 522, second marker conditions are set to create a second marker used for the second measurement. The second marker conditions set in the second measurement column 522 are different from the first marker conditions set in the first measurement column 521 in the following items: "AC" selected and input to set the abdominal circumference as a site to be measured second; "circle", which is a simple closed curve, selected and input to set the shape of the marker; "not display" selected and input not to display the position at which the measurement was made on the day of the previous examination; and "not display" selected and input not to display the normal range.

In third measurement column 523, third marker conditions are set to create a third marker used for the third measurement. The third marker conditions set in the third measurement column 523 are different from the first marker conditions set in the first measurement column 521 in the following items: "BPD" selected and input to set the biparietal diameter as a site to be measured third; "not display" selected and input not to display the position at which the measurement was made on the day of the previous examination; and "not display" selected and input not to display the normal range.

In the fourth measurement column 524, fourth marker conditions are set to create a fourth marker used for the fourth measurement. Because no site is measured other than the sites measured first to third, no marker conditions are set in the fourth measurement column 524 and subsequent columns, and the blank spaces are not filled.

FIG. 5 is a flowchart of an operation of the ultrasonic diagnostic apparatus 100. To perform an examination on the subject P, if the operating unit 80 inputs a 2D mode for creating two-dimensional image data and imaging conditions, and an operator presses an examination start button to input an instruction to start the examination, for example, the ultrasonic diagnostic apparatus 100 starts an operation (Step S1).

In response to the instruction to start the examination, the transmitting and receiving unit 20 drives the transducer elements of the ultrasonic probe 10 based on the input 2D mode and the imaging conditions. The transmitting and receiving unit 20 then performs phasing addition on received signals obtained by ultrasonic scanning performed on the subject P. The signal processing unit 21 processes the received signals subjected to phasing addition by the transmitting and receiving unit 20, thereby generating two-dimensional data. The image data generating unit 22 generates two-dimensional image data based on the two-dimensional data generated by the signal processing unit 21 (Step S2).

In response to the instruction to start the examination, the marker creating unit 30 creates the first to the third markers based on the information on the visual field depth included in the input imaging conditions, the number of weeks of pregnancy on the day of the previous examination and the day of the examination set on the examination registration screen 51 in FIG. 3, the first to the third marker conditions set on the marker condition setting screen 52 in FIG. 4, and the marker data stored in the data storage unit 23 (Step S3).

Figure 6:
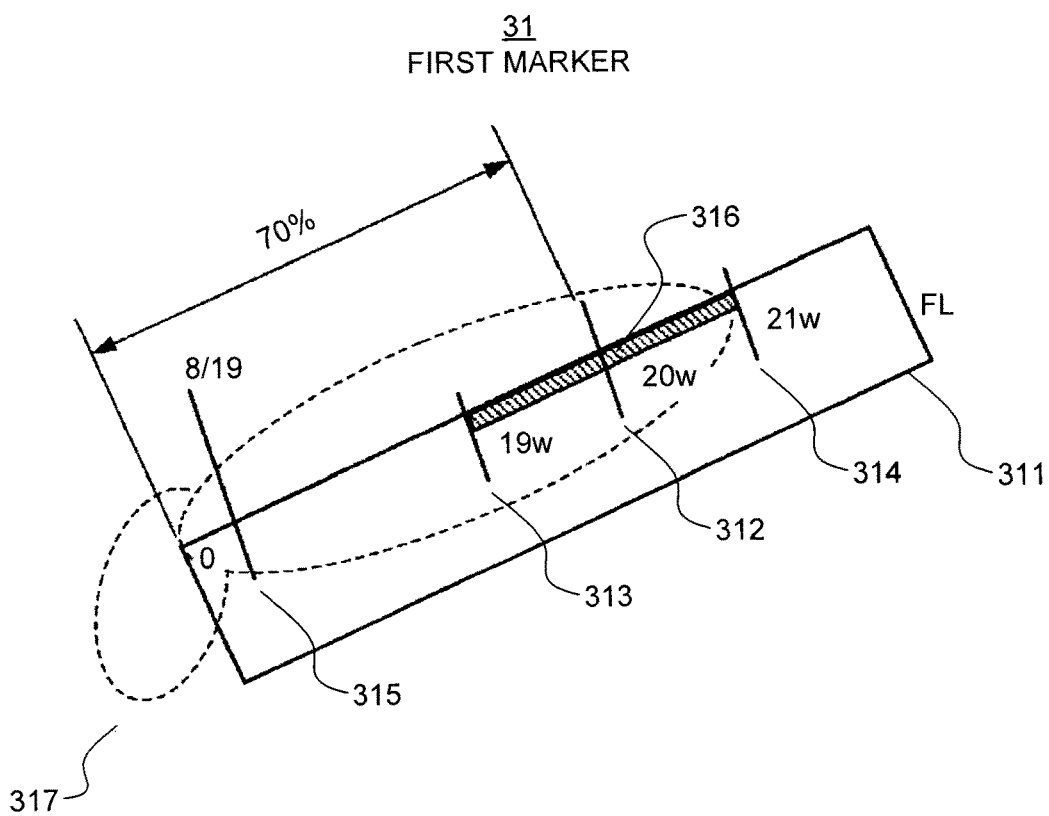
FIG. 6 is a schematic of an example of a first marker created by a marker creating unit according to the first embodiment.

FIG. 6 is a schematic of an example of the first marker created by the marker creating unit 30. First marker 31 is provided with "FL" indicating that the measurement item is the femur length and includes a marker body 311 having a rectangular shape corresponding to "straight line" set as the shape of the marker. The first marker 31 also includes four scale marks 312 to 315 between a first end and a second end of the marker body 311 in the longitudinal direction.

The first marker 31 has "0" indicating that the number of weeks of pregnancy is 0 on the first end of the marker body 311. The first marker 31 also has "20w" indicating that the number of weeks of pregnancy is 20 on the scale mark 312 provided correspondingly to the number of weeks of pregnancy on the day of the examination. The first marker 31 also has "19w" indicating that the number of weeks of pregnancy is 19 on the scale mark 313 provided correspondingly to the number of weeks of pregnancy of a week ago set as the number of weeks of pregnancy before the day of the examination.

The first marker 31 also has "21w" indicating that the number of weeks of pregnancy is 21 on the scale mark 314 provided correspondingly to the number of weeks of pregnancy of a week later set as the number of weeks of pregnancy after the day of the examination. The first marker 31 also has "8/19" indicating the date of the previous examination on the scale mark 315. The first marker 31 also includes a normal range 316 provided on the marker body 311 correspondingly to the number of weeks of pregnancy on the day of the examination.

In a case where the number of days is set as the unit of measurement in the first measurement column 521 of the marker condition setting screen 52, the number of days of pregnancy is displayed on the scale marks 312 to 314.

The scale marks 312 to 314 and the normal range 316 are determined based on the marker data of the author set on the marker condition setting screen 52 stored in the data storage unit 23 and on the information on the visual field depth. Assuming that the linear length between the first end and the second end of the marker body 311 is 100%, the scale mark 312 is arranged at a position of "70%" set as the position of the number of weeks of pregnancy on the day of the examination in the linear length from the first end.

The linear length between the scale mark 312 and the first end of the marker body 311 corresponds to the standard value of the femur length in the 20th week of pregnancy calculated based on the visual field depth and the standard value of the femur length in the 19th week of pregnancy. The linear length between the scale mark 313 and the first end of the marker body 311 corresponds to the standard value of the femur length in the 19th week of pregnancy calculated based on the visual field depth and the standard value of the femur length in the 19th week of pregnancy. The linear length between the scale mark 314 and the first end of the marker body 311 corresponds to the standard value of the femur length in the 21st week of pregnancy calculated based on the visual field depth and the standard value of the femur length in the 21st week of pregnancy. The linear length between the scale mark 315 and the first end of the marker body 311 corresponds to the femur length measured on the day of the previous examination calculated based on the visual field depth and the femur length measured on the day of the previous examination. The normal range 316 indicates that the range from the scale mark 313 to the scale mark 314 corresponds to the normal range of the femur length on the day of the examination, for example.

After creating the first marker 31, the marker creating unit 30 creates a posture guide 317 representing the femur to be measured with the first marker 31 as illustrated in FIG. 6. The marker creating unit 30 arranges the posture guide 317 such that an end of the posture guide 317 in the longitudinal direction substantially coincides with the first end of the first marker 31 and that the longitudinal direction of the posture guide 317 is parallel to that of the first marker 31.

Thus, the first marker 31 can be created with a simple operation of pressing the examination start button of the operating unit 80.

Figure 7:
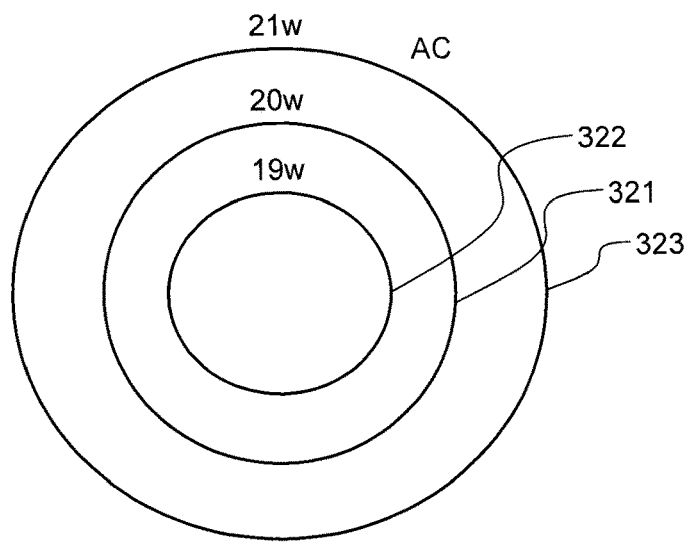
FIG. 7 is a schematic of an example of a second marker created by the marker creating unit according to the first embodiment.

FIG. 7 is a schematic of an example of the second marker created by the marker creating unit 30. Second marker 32 is provided with "AC" indicating that the measurement item is the abdominal circumference. The second marker 32 includes a scale mark 321, a scale mark 322 positioned on the inner side of the scale mark 321, and a scale mark 323 positioned on the outer side of the scale mark 321. The scale marks 321 to 323 are concentrically arranged correspondingly to "circle", which is a simple closed curve, set as the shape of the marker, for example. The second marker 32 has "20w" indicating that the number of weeks of pregnancy is 20 on the scale mark 321 provided correspondingly to the number of weeks of pregnancy on the day of the examination.

The second marker 32 also has "19w" indicating that the number of weeks of pregnancy is 19 on the scale mark 322 provided correspondingly to the number of weeks of pregnancy of a week ago set as the number of weeks of pregnancy before the day of the examination. The second marker 32 also has "21w" indicating that the number of weeks of pregnancy is 21 on the scale mark 323 provided correspondingly to the number of weeks of pregnancy of a week later set as the number of weeks of pregnancy after the day of the examination.

The scale markers 321 to 323 are determined based on the marker data of the author set on the marker condition setting screen 52 and the information on the visual field depth. The circumference of the scale marker 321 corresponds to the standard value of the abdominal circumference in the 20th week of the pregnancy. The circumference of the scale marker 322 corresponds to the standard value of the abdominal circumference in the 19th week of the pregnancy. The circumference of the scale marker 323 corresponds to the standard value of the abdominal circumference in the 21st week of the pregnancy.

Thus, the second marker 32 can be created with a simple operation of pressing the examination start button of the operating unit 80.

The measurement item may be the diameter of the abdomen in the longitudinal direction or the lateral direction. In this case, a circle may be set as the shape of the marker, for example, and the diameter of the set circle may be used as a scale mark corresponding to the standard value of the diameter of the abdomen in the longitudinal direction or the lateral direction.

Figure 8:
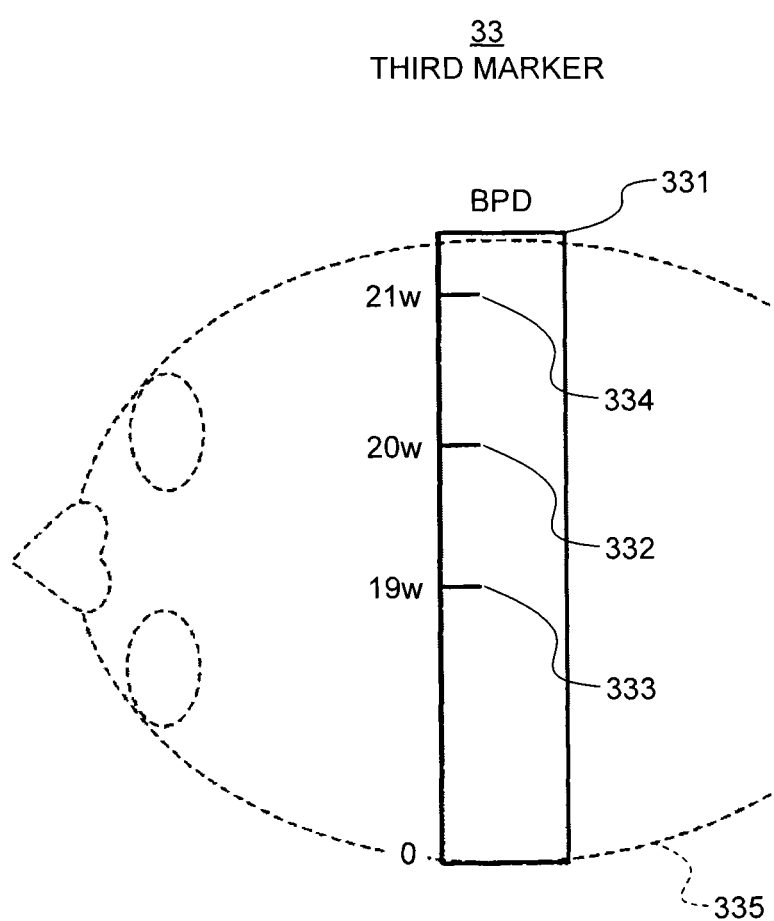
FIG. 8 is a schematic of an example of a third marker created by the marker creating unit according to the first embodiment.

FIG. 8 is a schematic of an example of the third marker created by the marker creating unit 30. Third marker 33 is provided with "BPD" indicating that the measurement item is the biparietal diameter and includes a marker body 331 having a rectangular shape corresponding to "straight line" set as the shape of the marker. The third marker 33 also includes three scale marks 332 to 334 between a first end and a second end of the marker body 331 in the longitudinal direction. The third marker 33 has "0" indicating that the number of weeks of pregnancy is 0 on the first end of the marker body 331.

The third marker 33 has "20w" indicating that the number of weeks of pregnancy is 20 on the scale mark 332 provided correspondingly to the number of weeks of pregnancy on the day of the examination. The third marker 33 also has "19w" indicating that the number of weeks of pregnancy is 19 on the scale mark 333 provided correspondingly to the number of weeks of pregnancy of a week ago set as the number of weeks of pregnancy before the day of the examination. The third marker 33 also has "21w" indicating that the number of weeks of pregnancy is 21 on the scale mark 334 provided correspondingly to the number of weeks of pregnancy of a week later set as the number of weeks of pregnancy after the day of the examination.

The scale marks 332 to 334 are determined based on the marker data of the author set on the marker condition setting screen 52 and the information on the visual field depth. Assuming that the linear length between the first end and the second end of the marker body 331 is 100%, the scale mark 332 is arranged at a position of "70%" set as the position of the number of weeks of pregnancy on the day of the examination in the linear length from the first end.

The linear length between the scale mark 332 and the first end of the marker body 331 corresponds to the standard value of the biparietal diameter in the 20th week of pregnancy. The linear length between the scale mark 333 and the first end of the marker body 331 corresponds to the standard value of the biparietal diameter in the 19th week of pregnancy. The linear length between the scale mark 334 and the first end of the marker body 331 corresponds to the standard value of the biparietal diameter in the 21st week of pregnancy.

Thus, the third marker 33 can be created with a simple operation of pressing the examination start button of the operating unit 80.

After creating the third marker 33, the marker creating unit 30 creates a posture guide 335 representing the head to be measured with the third marker 33 as illustrated in FIG. 8. The marker creating unit 30 arranges the posture guide 335 such that an end of the posture guide 335 used for the measurement substantially coincides with the first end of the third marker 33 and that the measurement direction of the posture guide 335 is parallel to the longitudinal direction of the third marker 33.

The marker creating unit 30 removes the posture guide 317 from the first marker 31 used for the first measurement. The synthesizing unit 40 synthesizes the two-dimensional image data generated by the image data generating unit 22 and the first marker 31 to the third marker 33 and the posture guide 335 created by the marker creating unit 30. In this example, the synthesizing unit 40 superimposes the first marker 31 used for the first measurement on the two-dimensional image data. The synthesizing unit 40 arranges the two-dimensional image data on which the first marker 31 is superimposed, the second marker 32, the third marker 33, and the posture guide 335 side by side.

The display 50 substantially simultaneously displays the two-dimensional image data and the marker including the first marker 31 to the third marker 33 and the posture guide 335 synthesized by the synthesizing unit 40 (Step S4 in FIG. 5).

Figure 9:
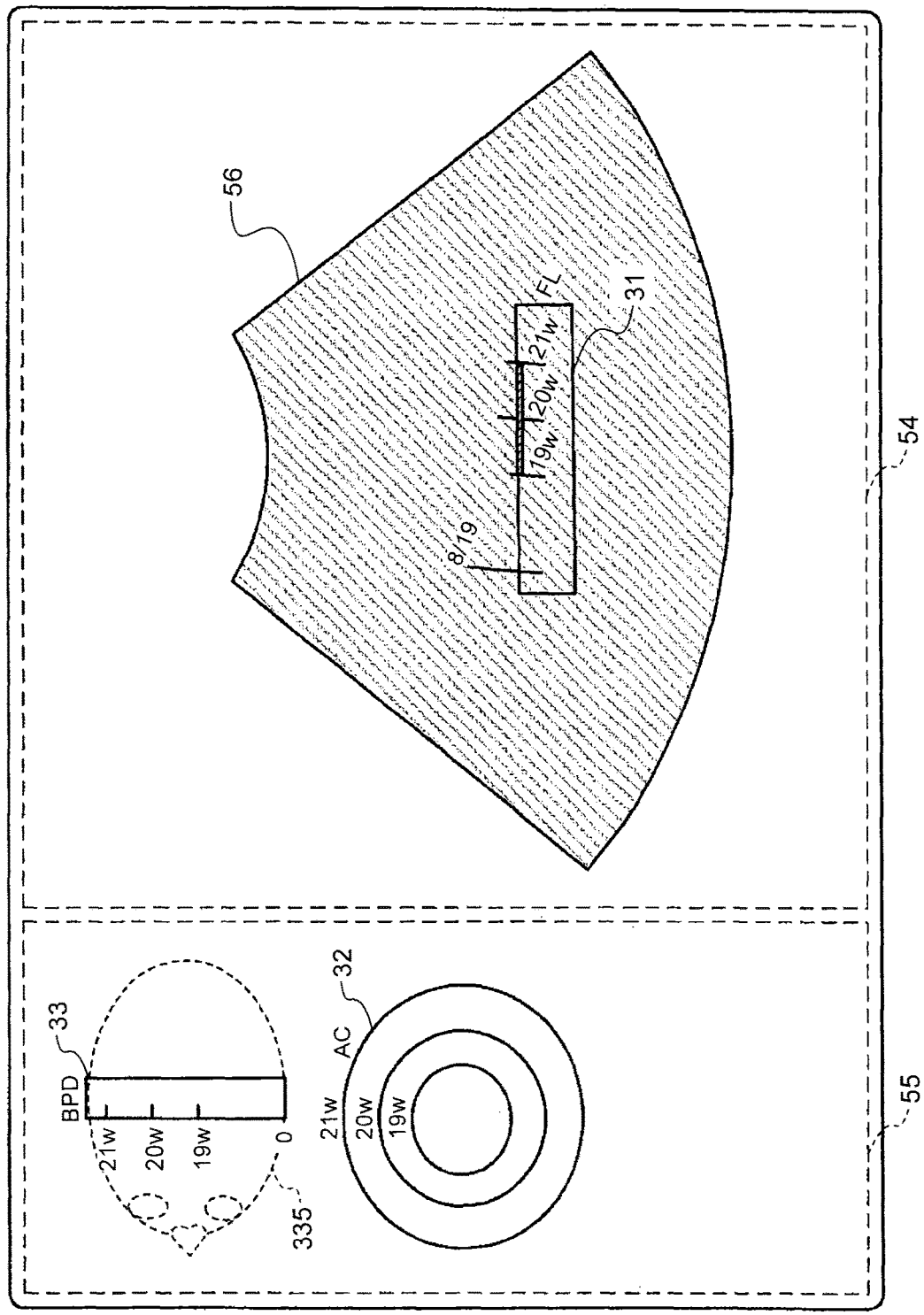
FIG. 9 is a schematic of an example of a screen that displays two-dimensional image data, the first to the third markers, and a posture guide on the display according to the first embodiment.

FIG. 9 is a schematic of an example of a screen that displays the two-dimensional image data, the first marker 31 to the third marker 33, and the posture guide 335 on the display 50. A screen 53 includes a first display area 54 and a second display area 55. The first display area 54 displays two-dimensional image data 56 in real time, and the first marker 31 is superimposed and displayed on the two-dimensional image data 56. The second display area 55 displays the second marker 32, the third marker 33, and the posture guide 335.

Thus, the display 50 substantially simultaneously displays the two-dimensional image data 56 and the first marker 31 to the third marker 33 with a simple operation of pressing the examination start button of the operating unit 80. Furthermore, the display 50 superimposes and displays the first marker 31 used for the first measurement on the two-dimensional image data 56 displayed on the display 50 in real time.

If the operating unit 80 inputs an instruction to change the visual field depth after the display 50 displays the two-dimensional image data 56, the first marker 31 to the third marker 33, and the posture guide 335 (Yes at Step S5 in FIG. 5), the process is returned to Step S2 and Step S3 in FIG. 5. If the operating unit 80 inputs no instruction to change the visual field depth (No at Step S5 in FIG. 5), the process proceeds to Step S6 in FIG. 5.

Figure 10:
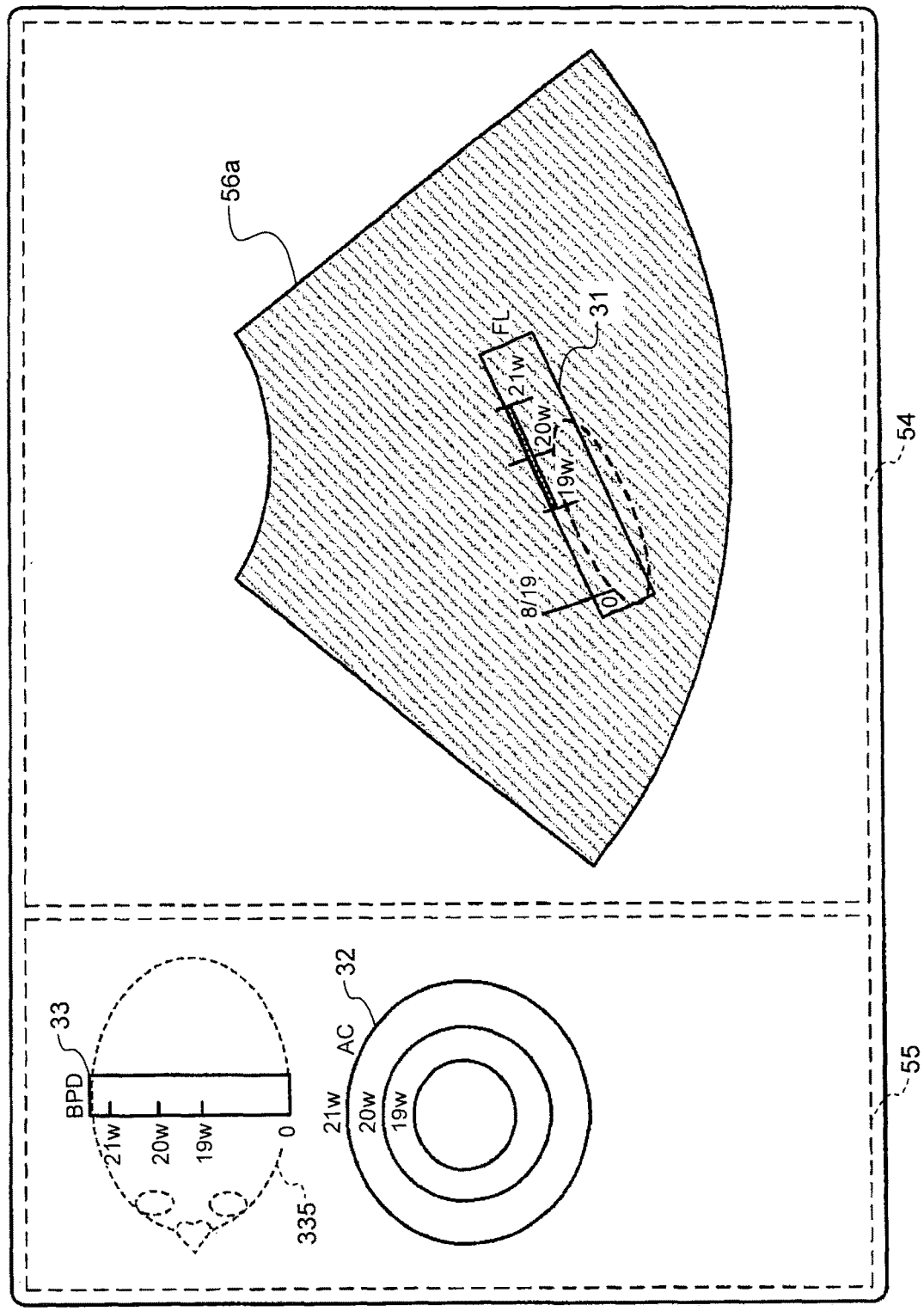
FIG. 10 is a schematic of an example of the first marker aligned with a region of interest on the two-dimensional image data according to the first embodiment.

The operator moves the ultrasonic probe 10 with the ultrasonic probe 10 in contact with the subject P. The operator stops the ultrasonic probe 10 at a position where the two-dimensional image data including data of the femoral region of the fetus is displayed. Subsequently, the operator operates a pointing device, such as a trackball, of the operating unit 80, thereby moving the first marker 31 in vertical and horizontal directions and in a rotation direction. Thus, the operator aligns the first marker 31 with the femoral region, which is indicated by the dashed line, corresponding to the region of interest on two-dimensional image data 56*a* displayed on the first display area 54 of a screen 53*a* in real time as illustrated in FIG. 10.

Thus, the femur of the fetus can be measured with a simple operation of the operating unit 80 aligning the first marker 31 with the femoral region on the two-dimensional image data 56*a* displayed on the display 50 in real time.

In this example, the first marker 31 is aligned such that one end of the femoral region in the longitudinal direction substantially coincides with the first end of the first marker 31 and that the longitudinal direction of the femoral region is parallel to that of the first marker 31.

In a case where the other end of the femoral region is positioned between the two scale marks 312 and 314 of the first marker 31, that is, within the normal range 316, for example, the operator can readily grasp that the femur of the fetus in the subject P in the 20th week of pregnancy is in a growth state between the 20th and the 21st weeks of pregnancy and is normally growing.

If the operating unit 80 inputs an instruction to store the first measurement data after the first marker 31 is aligned, the data storage unit 23 stores therein the two-dimensional image data 56*a* and the first marker 31 aligned on the two-dimensional image data 56*a* (Step S6 in FIG. 5).

In response to the instruction to store the first measurement data input from the operating unit 80, the synthesizing unit 40 synthesizes the two-dimensional image data generated by the image data generating unit 22, the first marker 31 to the third marker 33, and the posture guides 317 and 335. In this example, the synthesizing unit 40 superimposes the second marker 32 used for the second measurement on the two-dimensional image data. The synthesizing unit 40 arranges the two-dimensional image data on which the second marker 32 is superimposed, the first marker 31, the third marker 33, and the posture guides 317 and 335 side by side. The display 50 substantially simultaneously displays the two-dimensional image data, the first marker 31 to the third marker 33, and the posture guides 317 and 335 synthesized by the synthesizing unit 40.

Figure 11:
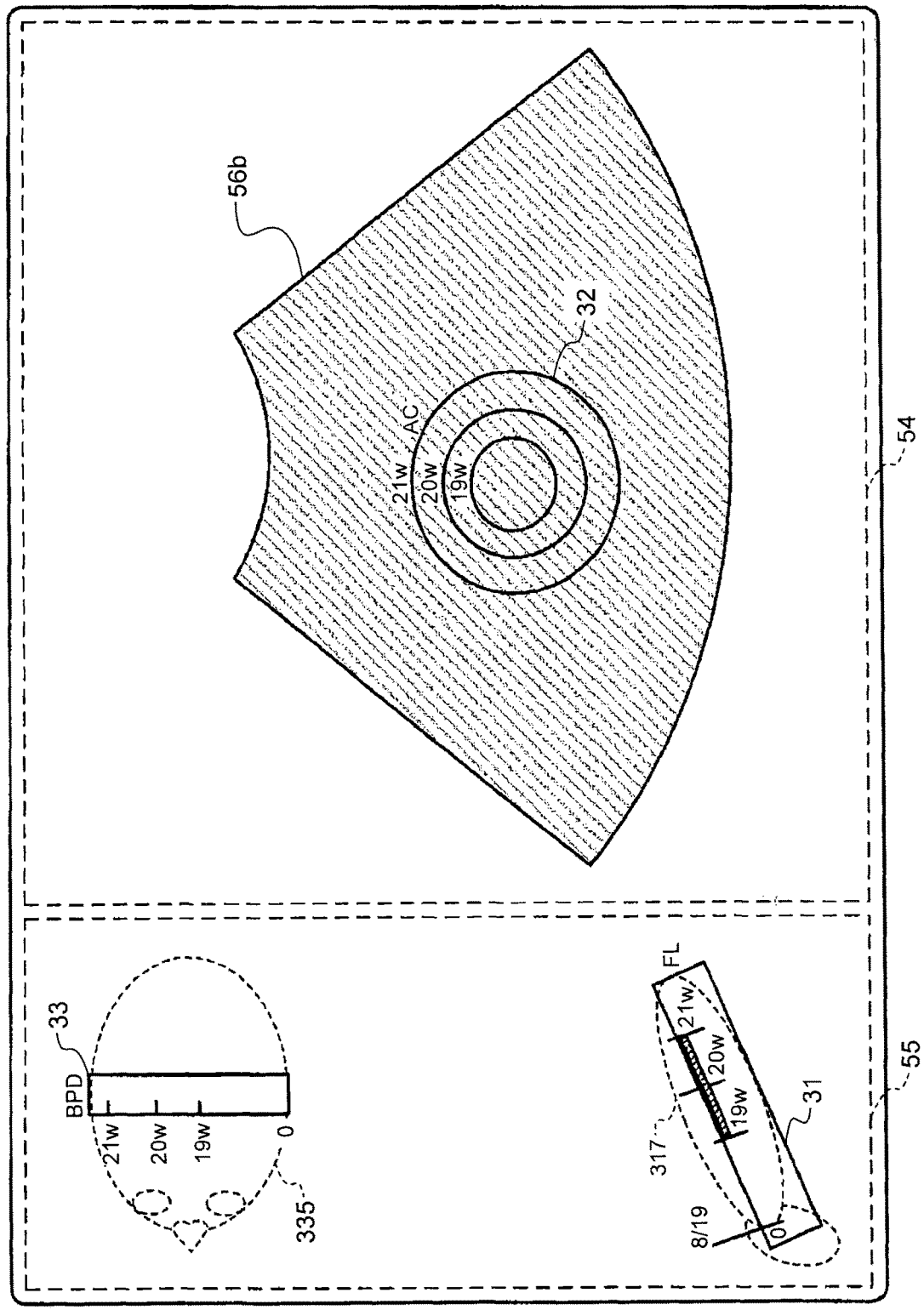
FIG. 11 is a schematic of an example of a screen that displays the two-dimensional image data, the first to the third markers, and the posture guides on the display in response to an instruction to store the first measurement data according to the first embodiment.

FIG. 11 is a schematic of an example of a screen that displays the two-dimensional image data, the first marker 31 to the third marker 33, and the posture guides 317 and 335 on the display 50 in response to an instruction to store the first measurement data. The first display area 54 of a screen 53*b* displays two-dimensional image data 56*b* in real time, and the second marker 32 is superimposed and displayed on the two-dimensional image data 56*b*. The second display area 55 displays the first marker 31, the third marker 33, and the posture guides 317 and 335.

In response to the instruction to store the first measurement data, the display 50 displays the two-dimensional image data 56*b* in real time together with the first marker 31 to the third marker 33. Furthermore, the display 50 superimposes and displays the second marker 32 used for the second measurement on the two-dimensional image data 56*b* displayed in real time. This mechanism can save the operator the trouble of moving the second marker 32 onto the two-dimensional image data 56*b*.

If the operating unit 80 inputs an instruction to print and output image data after the first marker 31 is aligned with the femoral region on the two-dimensional image data 56 at Step S6 in FIG. 5, the display 50 displays the screen 53*b* in response to the input.

Subsequently, an operation of moving the ultrasonic probe 10 causes the display 50 to display two-dimensional image data including the abdominal region in real time. If an instruction to store the second measurement data is input after the second marker 32 is aligned with the abdominal region on the two-dimensional image data, the data storage unit 23 stores therein the two-dimensional image data and the second marker 32 aligned with the abdominal region.

Thus, the abdominal region can be measured with a simple operation of the operating unit 80 aligning the second marker 32 with the abdominal region on the two-dimensional image data displayed on the display 50 in real time. This mechanism enables the operator to readily grasp the growth state of the abdomen of the fetus.

In response to the instruction to store the second measurement data input from the operating unit 80, the synthesizing unit 40 superimposes the third marker 33 on the two-dimensional image data generated by the image data generating unit 22. The synthesizing unit 40 synthesizes the two-dimensional image data on which the third marker 33 is superimposed, the first marker 31, the second marker 32, and the posture guide 317 side by side. The display 50 displays the two-dimensional image data, the first marker 31 to the third marker 33, and the posture guide 317 synthesized by the synthesizing unit 40.

Figure 12:
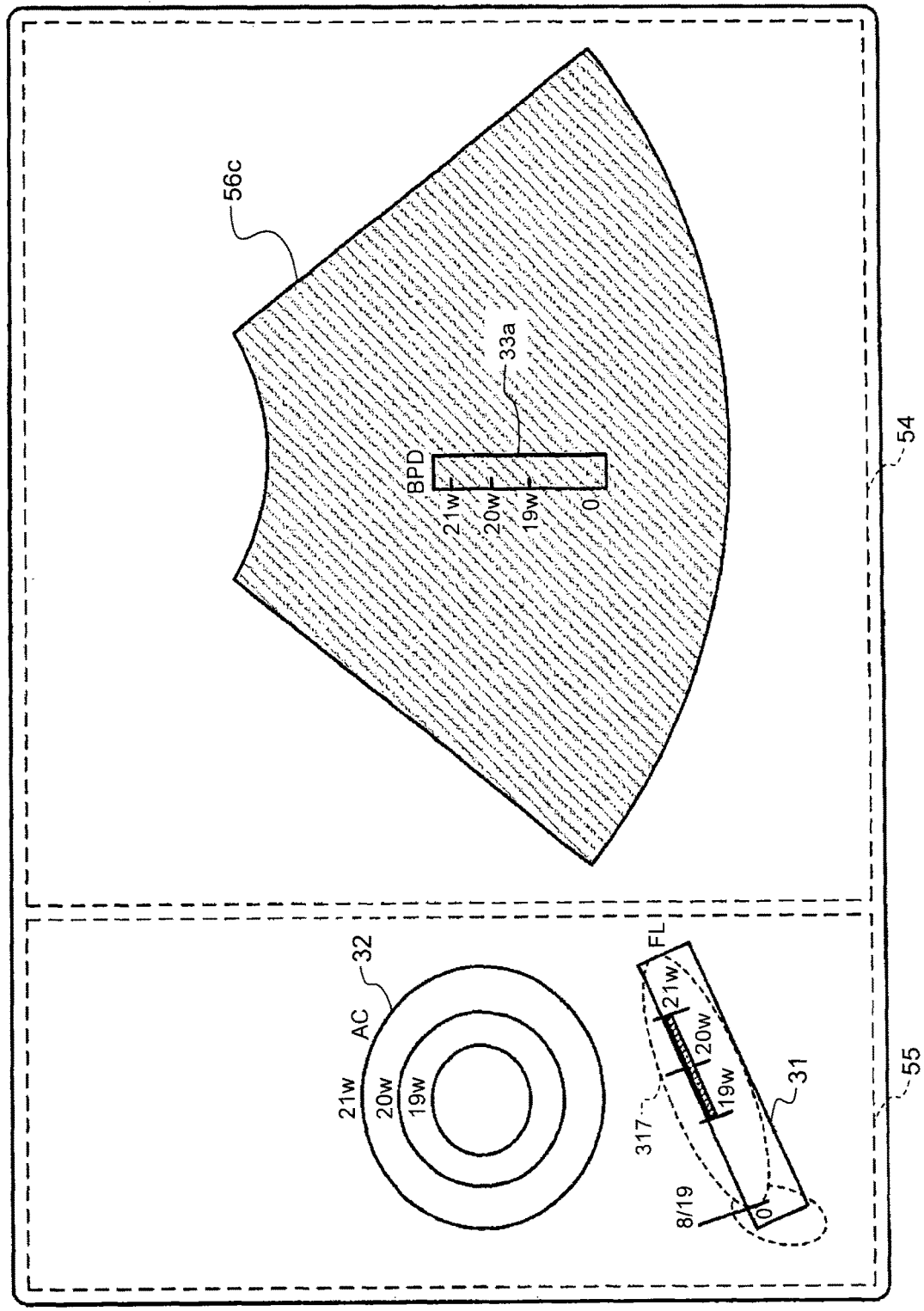
FIG. 12 is a schematic of an example of a screen that displays the two-dimensional image data, the first to the third markers, and the posture guide on the display in response to an instruction to store the second measurement data according to the first embodiment.

FIG. 12 is a schematic of an example of a screen that displays the two-dimensional image data, the first marker 31 to the third marker 33, and the posture guide 317 on the display 50 in response to an instruction to store the second measurement data. The first display area 54 of a screen 53*c* displays two-dimensional image data 56*c* in real time, and the third marker 33 is superimposed and displayed on the two-dimensional image data 56*c*. The second display area 55 displays the first marker 31, the second marker 32, and the posture guide 317.

In response to the instruction to store the second measurement data, the display 50 displays the two-dimensional image data 56*c* in real time together with the first marker 31 to the third marker 33. Furthermore, the display 50 superimposes and displays the third marker 33 used for the third measurement on the two-dimensional image data 56*c* displayed in real time. This mechanism can save the operator the trouble of moving the third marker 33 onto the two-dimensional image data 56c.

Subsequently, an operation of moving the ultrasonic probe 10 causes the display 50 to display two-dimensional image data including the head region in real time. If an instruction to store the third measurement data is input after the third marker 33 is aligned with the head region on the two-dimensional image data, the data storage unit 23 stores therein the two-dimensional image data and the third marker 33 aligned with the head region.

Thus, the head region can be measured with a simple operation of the operating unit 80 aligning the third marker 33 with the head region on the two-dimensional image data displayed on the display 50 in real time. This mechanism enables the operator to readily grasp the growth state of the head of the fetus.

In response to the instruction to store the third measurement data, the synthesizing unit 40 synthesizes the two-dimensional image data generated by the image data generating unit 22, the first marker 31 to the second marker 33, and the posture guides 317 and 335 side by side. The display 50 displays the two-dimensional image data, the first marker 31 to the third marker 33, and the posture guides 317 and 335 synthesized by the synthesizing unit 40.

Figure 13:
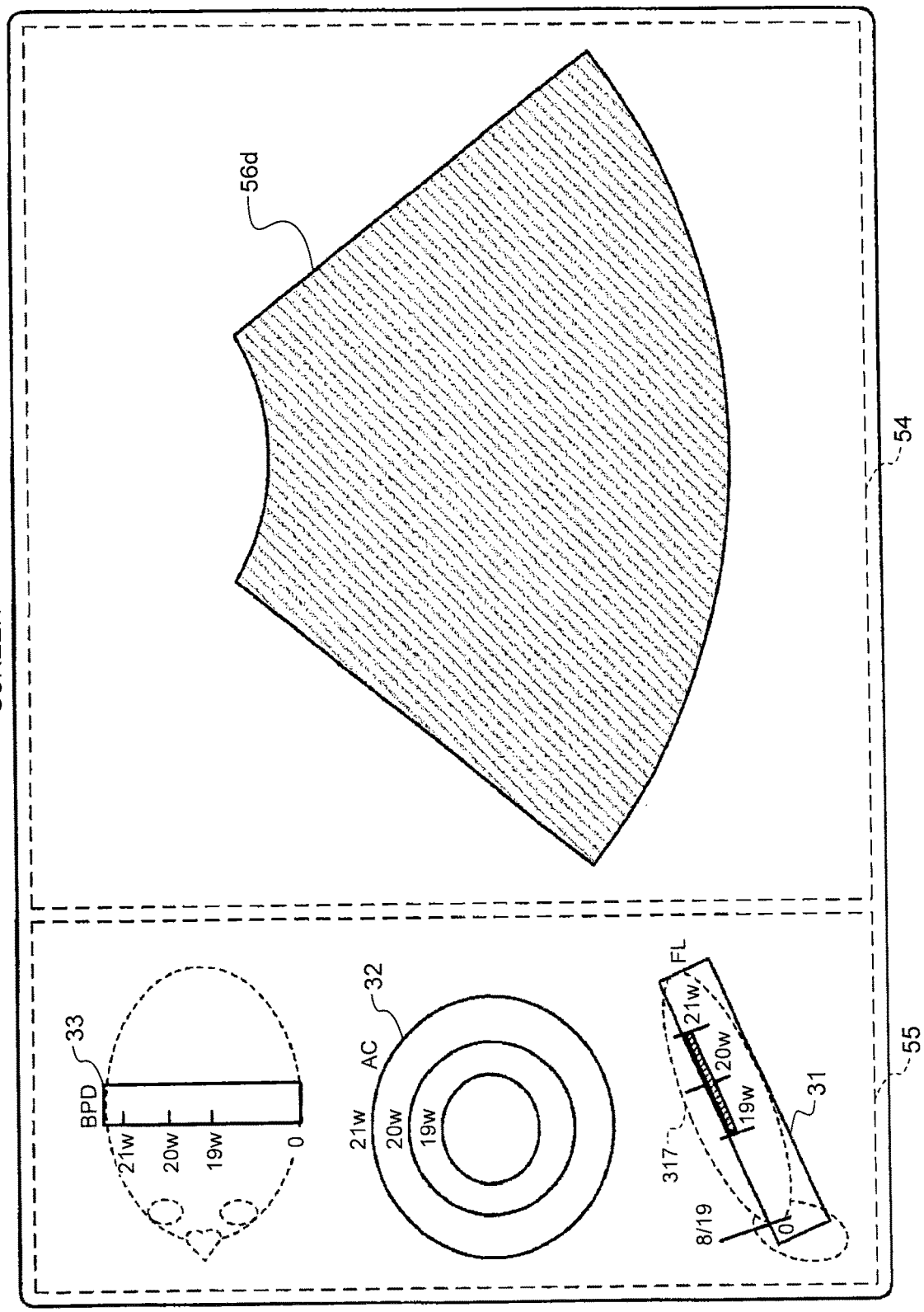
FIG. 13 is a schematic of an example of a screen that displays the two-dimensional image data, the first to the third markers, and the posture guides on the display in response to an instruction to store the third measurement data according to the first embodiment.

FIG. 13 is a schematic of an example of a screen that displays the two-dimensional image data, the first marker 31 to the third marker 33, and the posture guides 317 and 335 on the display 50 in response to an instruction to store the third measurement data. The first display area 54 of a screen 53d displays two-dimensional image data 56d in real time. The second display area 55 displays the first marker 31 to the third marker 33 and the posture guides 317 and 335.

If the operating unit 80 inputs an instruction to end the examination, the system control unit 90 stops the operation of the transmitting and receiving unit 20, the signal processing unit 21, the image data generating unit 22, the data storage unit 23, the marker creating unit 30, the synthesizing unit 40, and the display 50. Thus, the ultrasonic diagnostic apparatus 100 terminates the operation (Step S7 in FIG. 5).

According to the embodiment above, the display 50 simultaneously displays the two-dimensional image data 56 and the first marker 31 to the third marker 33 with a simple operation of pressing the examination start button of the operating unit 80. Furthermore, the display 50 superimposes and displays the first marker 31 used for the first measurement on the two-dimensional image data 56 displayed on the display 50 in real time.

The femoral region can be measured with a simple operation of the operating unit 80 aligning the first marker 31 with the femoral region on the two-dimensional image data 56a displayed in real time. In a case where the femoral region on the two-dimensional image data 56a is positioned between the two scale marks 312 and 314 of the first marker 31, that is, within the normal range 316, for example, the operator can readily grasp that the femur of the fetus in the subject P is in a growth state between the 20th and the 21st weeks of pregnancy and is normally growing.

In response to an instruction to store the first measurement data, the data storage unit 23 stores therein the two-dimensional image data 56a and the first marker 31 aligned with the femoral region. The display 50 displays the two-dimensional image data 56b in real time together with the first marker 31 to the third marker 33. Furthermore, the display 50 superimposes and displays the second marker 32 used for the second measurement on the two-dimensional image data 56b. This mechanism can save the operator the trouble of moving the second marker 32 onto the two-dimensional image data 56b.

The abdominal region can be measured with a simple operation of the operating unit 80 aligning the second marker 32 with the abdominal region on the two-dimensional image data displayed on the display 50 in real time. This mechanism enables the operator to readily grasp the growth state of the abdomen of the fetus.

In response to an instruction to store the second measurement data, the data storage unit 23 stores therein the two-dimensional image data and the second marker 32 aligned with the abdominal region. The display 50 displays the two-dimensional image data 56c in real time together with the first marker 31 to the third marker 33. Furthermore, the display 50 superimposes and displays the third marker 33 used for the third measurement on the two-dimensional image data 56c. This mechanism can save the operator the trouble of moving the third marker 33 onto the two-dimensional image data 56c.

The head region can be measured with a simple operation of the operating unit 80 aligning the third marker 33 with the head region on the two-dimensional image data displayed on the display 50 in real time. This mechanism enables the operator to readily grasp the growth state of the head of the fetus. In response to an instruction to store the third measurement data, the data storage unit 23 stores therein the two-dimensional image data and the third marker 33 aligned with the head region.

As described above, the first embodiment can measure the fetus in the subject P with a simple operation, thereby reducing the amount of work in the examination.

Modification of the First Embodiment

Figure 14:
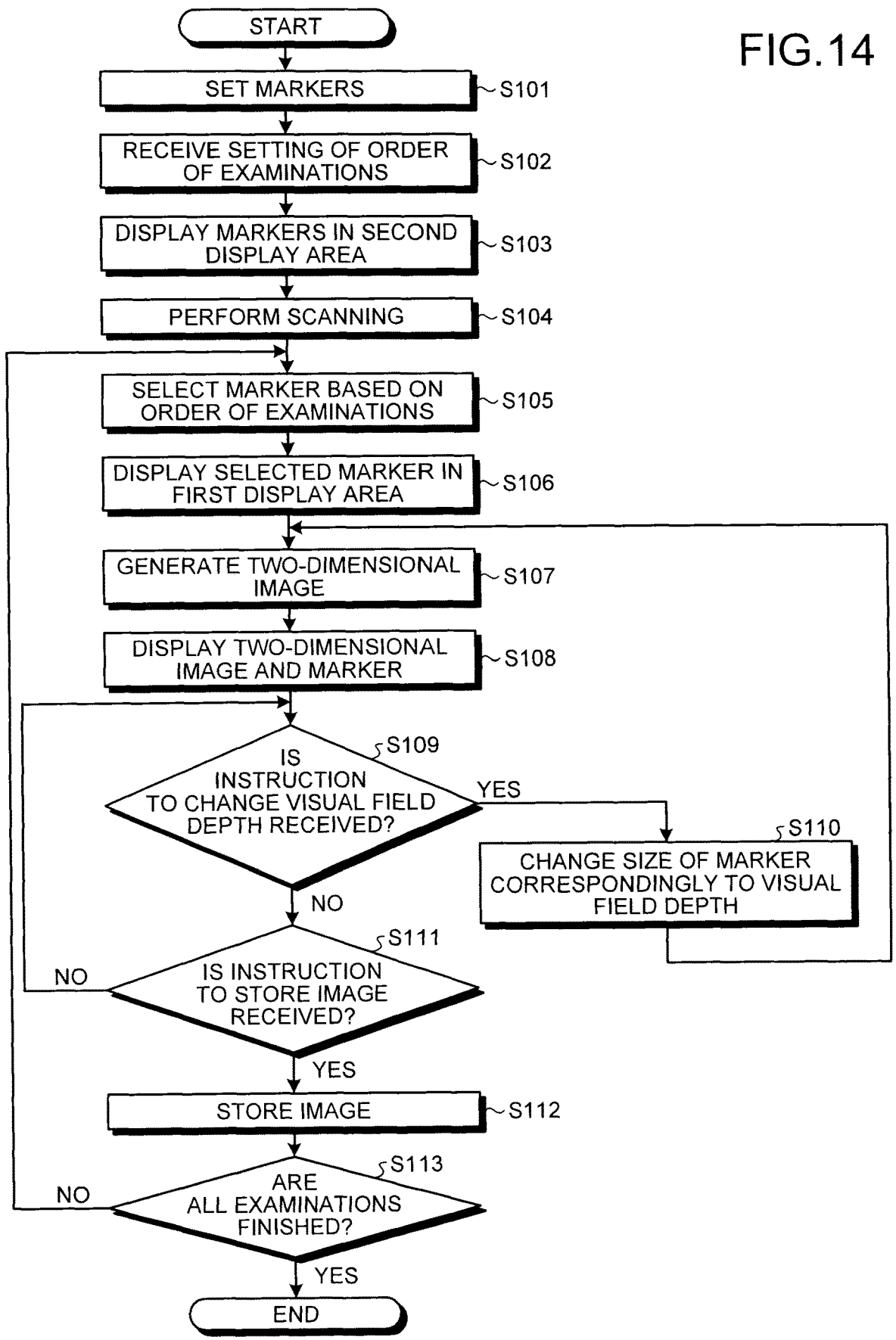
FIG. 14 is a flowchart of a process performed by the ultrasonic diagnostic apparatus according to a modification of the first embodiment.

The process performed by the ultrasonic diagnostic apparatus 100 according to the first embodiment is not limited to the process illustrated in FIG. 5. The following describes a process performed by the ultrasonic diagnostic apparatus according to a modification of the first embodiment with reference to FIG. 14. FIG. 14 is a flowchart of a process performed by the ultrasonic diagnostic apparatus according to the modification of the first embodiment.

As illustrated in FIG. 14, the marker creating unit 30 creates markers similarly to the processing at Step S3 in FIG. 5 (Step S101). In other words, the marker creating unit 30 creates the markers based on the information on the visual field depth included in the input imaging conditions, the number of weeks of pregnancy on the day of the previous examination and the day of the examination set on the examination registration screen 51 in FIG. 3, the marker conditions set on the marker condition setting screen 52 in FIG. 4, and the marker data stored in the data storage unit 23. In this example, the marker creating unit 30 creates the first marker 31, the second marker 32, and the third marker 33.

The system control unit 90 receives setting of the order of examinations (Step S102). The system control unit 90, for example, determines to perform the examinations in order from the top of the measurement items displayed on the marker condition setting screen 52 in FIG. 4. In the state illustrated in FIG. 4, the system control unit 90 determines to perform the examinations in order of a measurement item 1, a measurement item 2, and a measurement item 3. In a case where the order of the measurement items is changed on the marker condition setting screen 52, the system control unit 90 determines to perform the examinations in the order resulting from the change. In other words, the system control unit 90 sets the order of examinations in advance. The following describes a case where the system control unit 90 determines to perform the examinations in order of the first marker 31, the second marker 32, and the third marker 33.

The display 50 displays the markers in the second display area 55 under the control of the system control unit 90 (Step S103). The display 50, for example, displays the first marker 31, the second marker 32, and the third marker 33 in the second display area 55. In other words, the system control unit 90 causes the display 50 to display the markers after the operation of setting the examination information is finished. After the display 50 displays the markers in the second display area 55, the system control unit 90 accepts execution of scanning (Step S104).

Thus, the system control unit 90 selects a marker based on the order of examinations (Step S105). Immediately after the scanning is started, for example, the system control unit 90 selects the first marker 31. The display 50 displays the marker selected by the system control unit 90 in the first display area 54 (Step S106).

The image data generating unit 22 generates a two-dimensional image similarly to the processing at Step S2 in FIG. 5 (Step S107). The display 50 displays the two-dimensional image and the marker synthesized by the synthesizing unit 40 (Step S108). In other words, the system control unit 90 displays the marker before the display 50 displays the image. The system control unit 90 displays, when the image data generating unit 22 generates a new image, the new image on the display 50 as a substitute for an old image previously displayed on the display 50 without changing display of the marker.

The system control unit 90 determines whether it has received an instruction to change the visual field depth (Step S109). If the system control unit 90 determines that it has received an instruction to change the visual field depth (Yes at Step S109), the marker creating unit 30 changes the size of the marker displayed in the first display area 54 into the size of the marker corresponding to the visual field depth (Step S110). In other words, the marker creating unit 30 determines the position to which the information is provided based on the visual field depth in the transmission and reception directions of the ultrasonic waves included in the imaging conditions for the scanning. After the processing at Step S110, the process is returned to Step S107.

By contrast, if the system control unit 90 determines that it has received no instruction to change the visual field depth (No at Step S109), the system control unit 90 determines whether it has received an instruction to store the image (Step S111). If the system control unit 90 determines that it has received no instruction to store the image (No at Step S111), the process is returned to Step S109, and the system control unit 90 determines whether it has received an instruction to change the visual field depth.

By contrast, if the system control unit 90 determines that it has received an instruction to store the image (Yes at Step S111), the system control unit 90 stores the image (Step S112). Subsequently, the system control unit 90 determines whether all the examinations are finished (Step S113). If the system control unit 90 determines that all the examinations are finished (Yes at Step S113), the system control unit 90 terminates the processing. By contrast, if the system control unit 90 determines that all the examinations are not finished (No at Step S113), the process is returned to Step S105. Thus, a marker is selected based on the order of examinations, and the selected marker is displayed in the first display area 54. In other words, if an image is stored, the first display area 54 automatically displays a marker for an examination subsequent to the examination in which the image is stored.

While the system control unit 90 receives the setting of the order of examinations on the marker condition setting screen 52 in FIG. 14, the embodiment is not limited thereto. The system control unit 90, for example, may set the order of examinations by changing the positions of the markers in the second display area 55 based on an instruction issued by the operator. The system control unit 90, for example, determines to perform the examinations in order from the top of the markers displayed in the second display area 55.

While the system control unit 90, if it accepts execution of scanning, selects a marker based on the order of examinations and displays the selected marker in the first display area 54 in FIG. 14, the embodiment is not limited thereto. The position of the marker on display, for example, may be changed based on an instruction issued by the operator. More specifically, the system control unit 90 may display a marker selected by the operator in the first display area 54 out of the markers displayed in the second display area 55.

The form and the shape of the markers may be changed between the case where they are displayed in the second display area 55 and the case where they are displayed in the first display area 54. The first display area 54, for example, may display no posture guide. Alternatively, the first display area 54 may display a posture guide.

The marker creating unit 30 may create an identification marker and an observation marker. The identification marker is displayed in the second display area 55 of the display 50, whereas the observation marker corresponds to the identification marker and is displayed in the first display area 54 of the display 50. The system control unit 90 displays the identification marker in the second display area 55. If the second marker is selected, the system control unit 90 displays the observation marker in the first display area 54.

Figure 15:
FIG. 15 is a schematic of an example of a marker according to the modification of the first embodiment.
Figure 16:
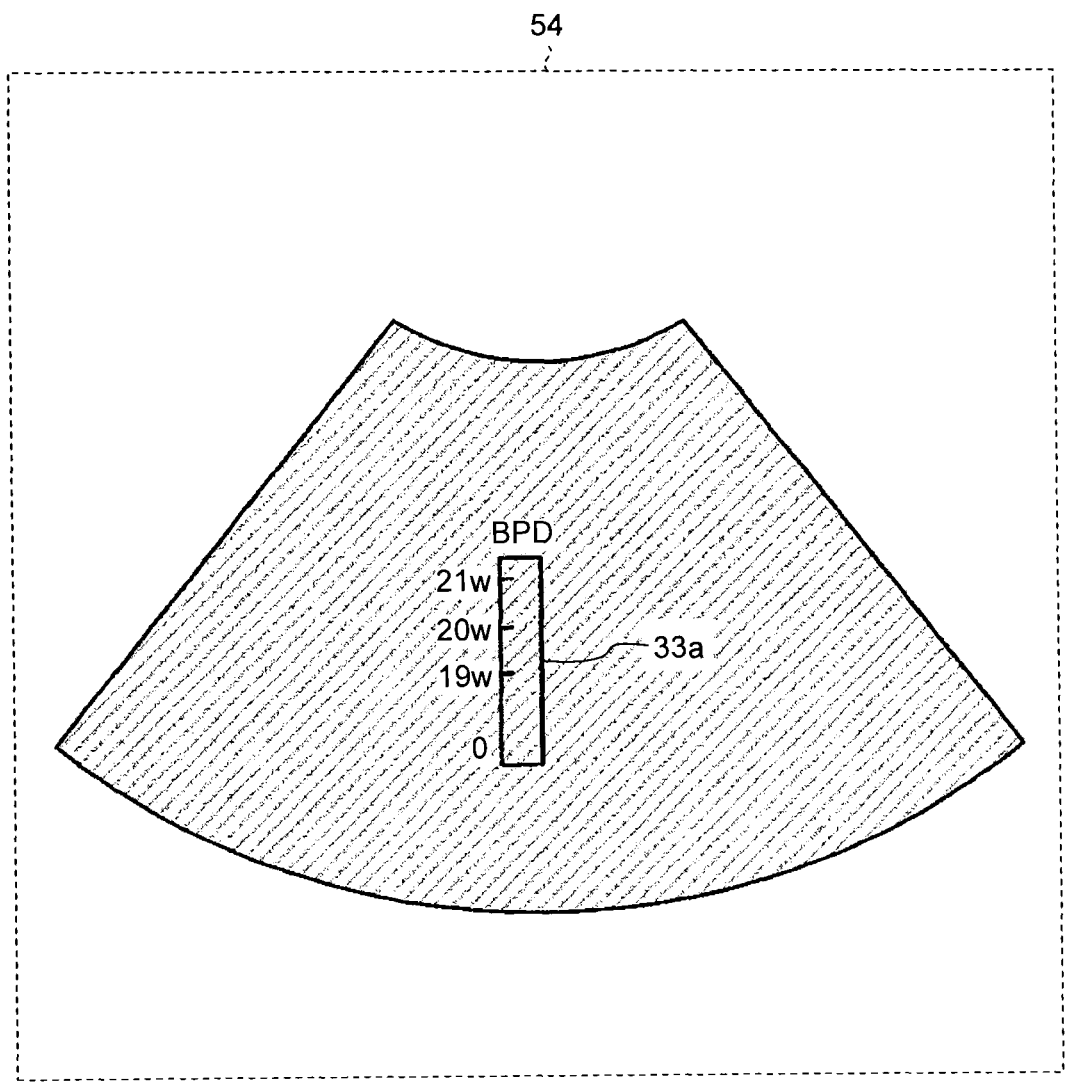
FIG. 16 is a schematic of an example of another marker according to the modification of the first embodiment.

FIGS. 15 and 16 are schematics of examples of markers according to the modification of the first embodiment. FIG. 15 illustrates an example of the identification marker displayed in the second display area 55 of the display 50. FIG. 16 illustrates an example of the observation marker displayed in the first display area 54 of the display 50. In FIGS. 15 and 16, the markers are used for measurement of the biparietal diameter. As illustrated in FIG. 15, for example, the marker creating unit 30 generates an identification marker 33 including a posture guide 33S indicating a region including the head of a fetus. As described above, the marker creating unit 30 generates the identification marker 33 including the posture guide 33S indicating an examined site and the positional relation of the marker on the examined site. As a result, the operator can readily grasp the examination to be performed.

In a case where the identification marker 33 is selected, the system control unit 90 displays an observation marker 33a illustrated in FIG. 16 in the first display area 54. The observation marker 33a does not include the posture guide 33S illustrated in FIG. 15. This mechanism enables the operator to align the observation marker 33a with the measured site and perform the examination while preventing the posture guide 33S from reducing the visibility of the two-dimensional image. While displaying the observation marker 33a in the first display area 54, the system control unit 90 may display the identification marker 33 corresponding to the observation marker 33a in the second display area 55.

While the femur, the abdominal circumference, and the biparietal diameter are measured as certain structures according to the first embodiment, the embodiment is not limited thereto. The certain structure may be a plaque formed in a tumor or a blood vessel, for example. In this case, the marker has information at a position to determine the appropriateness of the certain structure.

Figure 17:
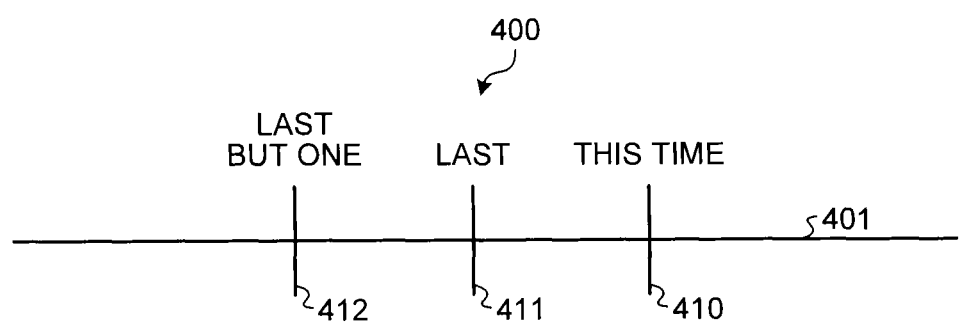
FIG. 17 is a schematic of an example of still another marker according to the modification of the first embodiment.
Figure 18:
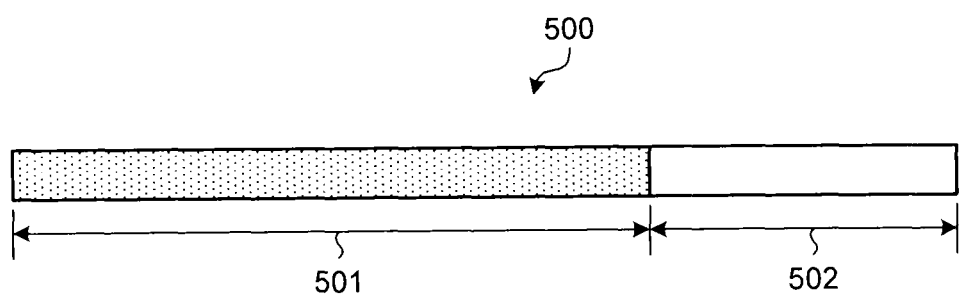
FIG. 18 is a schematic of an example of still another marker according to the modification of the first embodiment.

FIGS. 17 and 18 are schematics of examples of markers according to the modification of the first embodiment. FIG. 17 illustrates a scale used to determine the nature of a tumor. A marker 400 illustrated in FIG. 17 includes a marker body 401 having a linear shape corresponding to "straight line" set as the shape of the marker. The marker 400 also includes three scale marks 410 to 412 in the longitudinal direction of the marker body 401. The scale mark 411 includes characteristic information "last". "Last" indicates a position corresponding to the size of the tumor measured in the examination one time before the examination this time. The scale mark 412 includes characteristic information "last but one". "Last but one" indicates a position corresponding to the size of the tumor measured in the examination two times before the examination this time. The scale mark 410 includes characteristic information "this time". "This time" indicates a position corresponding to the size of the tumor provided correspondingly to an estimated growth degree of the tumor for the day of the examination. The growth degree of the tumor is calculated from the size of the tumor last time based on the size of the tumor measured last time and that measured last time but one. The operator can readily grasp whether the growth degree of the tumor is higher or lower than the estimated growth degree simply by measuring the tumor with the marker 400 and determining whether the size of the tumor exceeds the scale mark 410, for example.

FIG. 18 illustrates another example of the scale used to determine the nature of a tumor. A marker 500 illustrated in FIG. 18 has a rectangular shape corresponding to "straight line" set as the shape of the marker. The marker 500 includes a first area 501 and a second area 502. The first area 501 indicates that the growth degree of the tumor falls within a range of the estimated growth degree for the day of the examination. By contrast, the second area 502 indicates that the growth degree of the tumor is outside the range of the estimated growth degree for the day of the examination. The growth degree of the tumor is calculated from the size of the tumor last time based on the size of the tumor measured last time and that measured last time but one. The operator can readily grasp whether the growth degree of the tumor falls within the range of the estimated growth degree by measuring the tumor with the marker 500 and determining whether the size of the tumor exceeds the first area 501, for example. The first area 501 and the second area 502 of the marker may be displayed in different colors.

The marker creating unit 30 may generate a marker for comparison of the shape as the marker used to determine the appropriateness of the certain structure. The marker creating unit 30, for example, creates a marker having a shape similar to the normal shape of the certain structure. Thus, the operator can determine whether the shape of the measured certain structure is appropriate by making the measurement with the marker having a shape similar to the normal shape of the certain structure. The marker having a shape similar to the normal shape of the certain structure is statistically derived from clinical data on the certain structure. In other words, the marker creating unit 30 determines the position to which the information is provided based on an index value statistically calculated from clinical data on the certain structure.

Second Embodiment

While the medical image diagnostic apparatus according to the first embodiment is an ultrasonic diagnostic apparatus, the embodiment is not limited thereto. The growth of a fetus may be measured using a magnetic resonance imaging (MRI) apparatus, for example. Creation of a marker is also applicable to this case to reduce the amount of work in the examination with a simple operation. The second embodiment will describe creation of a marker performed by a medical image diagnostic apparatus other than the ultrasonic diagnostic apparatus.

The exemplary configuration of the medical image diagnostic apparatus according to the second embodiment is the same as that of the ultrasonic diagnostic apparatus 100 illustrated in FIG. 1 except that the configuration of the scanning unit and a part of the functions of the units other than the scanning unit are different from those according to the first embodiment. In other words, the medical image diagnostic apparatus according to the second embodiment includes the scanning unit 1, the signal processing unit 21, the image data generating unit 22, the data storage unit 23, the marker creating unit 30, the synthesizing unit 40, the display 50, the printing unit 60, the operating unit 80, and the system control unit 90. The synthesizing unit 40, for example, synthesizes image data generated by the image data generating unit 22 and a marker created by the marker creating unit 30. The display 50 includes a liquid-crystal panel, for example, and displays in real time the image data generated by the image data generating unit 22. The operating unit 80 includes an input device, such as a trackball and a switch. The operating unit 80 is used for an input of the imaging conditions, an input for setting the marker conditions, an input for setting the examination information, and an input for starting and ending an examination, for example.

In a case where the medical image diagnostic apparatus is an X-ray computed tomography (CT) apparatus, the signal processing unit 21 performs logarithmic transformation and correction, such as offset correction, sensitivity correction, and beam-hardening correction, on projection data generated by the scanning unit 1, which will be described later. Thus, the signal processing unit 21 generates corrected projection data. In a case where the medical image diagnostic apparatus is an X-ray CT apparatus, the data storage unit 23 stores therein the projection data generated by the signal processing unit 21. In a case where the medical image diagnostic apparatus is an X-ray CT apparatus, the image data generating unit 22 reconstructs X-ray CT image data using the projection data stored in the data storage unit 23.

Figure 19:
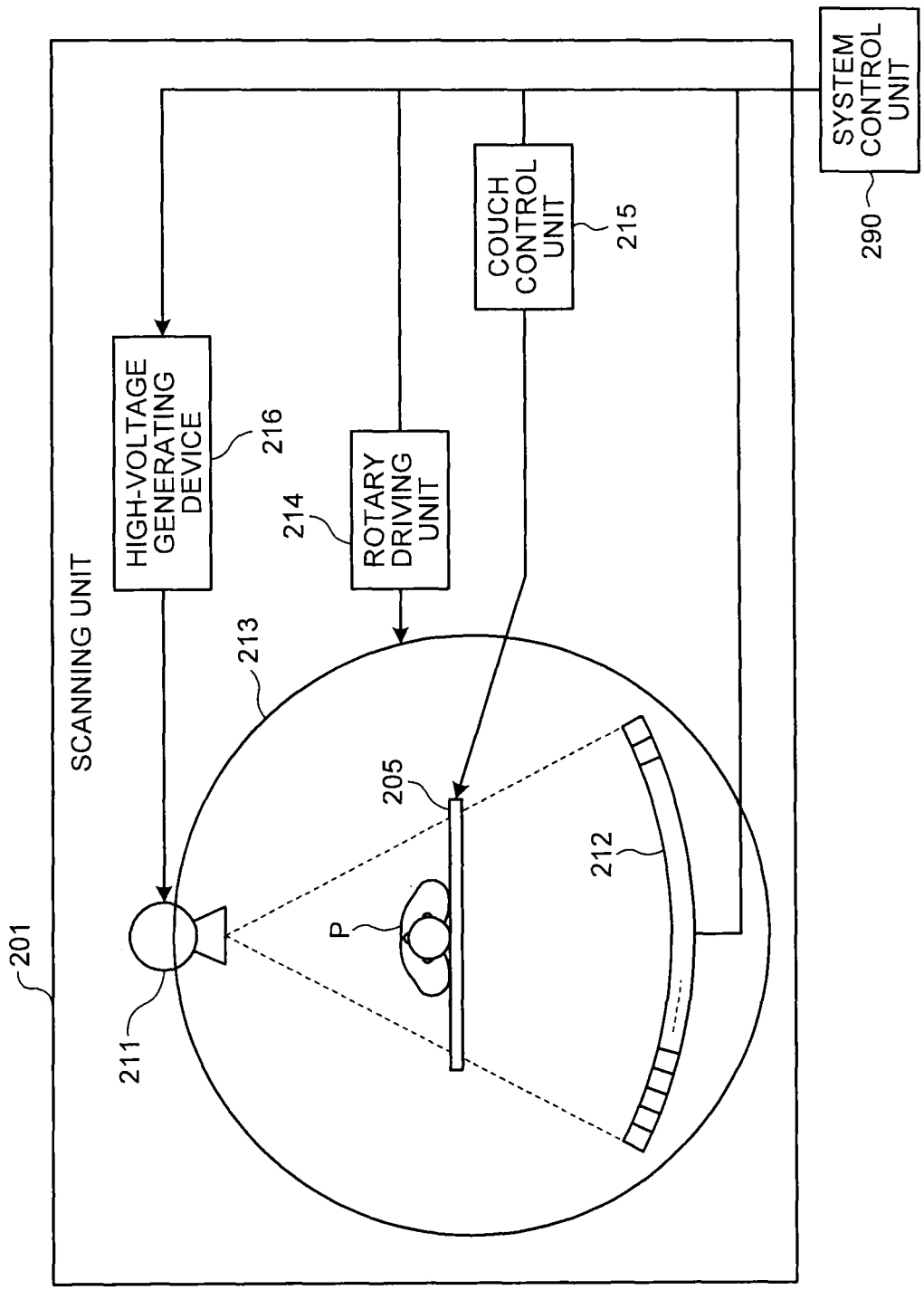
FIG. 19 is a diagram of an exemplary configuration of a scanning unit in a case where a medical image diagnostic apparatus according to a second embodiment is an X-ray CT apparatus.

The following describes the scanning unit 1 in a case where the medical image diagnostic apparatus is an X-ray CT apparatus, for example, with reference to FIG. 19. FIG. 19 is a diagram of an exemplary configuration of a scanning unit 201 in a case where the medical image diagnostic apparatus according to the second embodiment is an X-ray CT apparatus. FIG. 19 illustrates the scanning unit 1 in FIG. 1 as the scanning unit 201 and illustrates the system control unit 90 in FIG. 1 as a system control unit 290. The scanning unit 201 includes an X-ray tube 211 and an X-ray detector system 212. The X-ray tube 211 irradiates the subject P with X-rays. The X-ray detector system 212 detects X-rays passing through the subject P. The system control unit 290 collectively controls the X-ray CT apparatus. The system control unit 290 controls a rotary driving unit 214, a couch control unit 215, and a high-voltage generating device 216.

In a case where the medical image diagnostic apparatus is an MRI apparatus, the signal processing unit 21 reads MR data generated by the scanning unit 1, which will be described later, from the data storage unit 23. The signal processing unit 21 arranges the MR data in a k-space, thereby generating k-space data. In a case where the medical image diagnostic apparatus is an MRI apparatus, the data storage unit 23 stores therein MR data, k-space data, and MR image data generated by the image data generating unit 22, for example. In a case where the medical image diagnostic apparatus is an MRI apparatus, the image data generating unit 22 reads the k-space data stored in the data storage unit 23. The image data generating unit 22 performs reconstruction, such as two-dimensional Fourier transformation, on the read k-space data, thereby generating MR image data.

Figure 20:
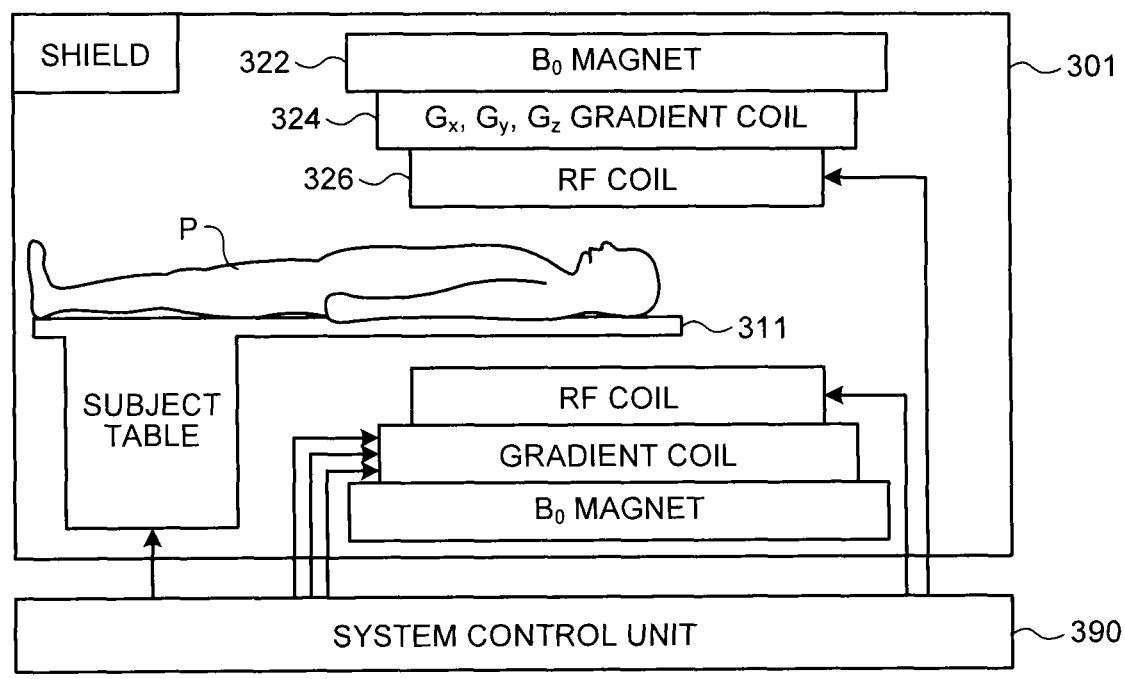
FIG. 20 is a diagram of an exemplary configuration of the scanning unit in a case where the medical image diagnostic apparatus according to the second embodiment is an MRI apparatus.

The following describes the scanning unit 1 in a case where the medical image diagnostic apparatus is an MRI apparatus, for example, with reference to FIG. 20. FIG. 20 is a diagram of an exemplary configuration of a scanning unit 301 in a case where the medical image diagnostic apparatus according to the second embodiment is an MRI apparatus. FIG. 20 illustrates the scanning unit 1 in FIG. 1 as the scanning unit 301 and illustrates the system control unit 90 in FIG. 1 as a system control unit 390. The scanning unit 301 includes a magnetostatic magnet 322, a gradient coil 324, a transmission coil 326, and a reception coil. The magnetostatic magnet 322 generates a static magnet field in the internal space. The gradient coil 314 generates a gradient magnetic field. The transmission coil 316 is arranged on the inner side of the gradient coil 314 and generates a high-frequency magnetic field. The reception coil is arranged on the inner side of the gradient coil 314 and receives magnetic resonance signals output from the subject P by the effect of the high-frequency magnetic field. The system control unit 390 collectively controls the MRI apparatus.

In the medical image diagnostic apparatus having the configuration described above according to the second embodiment, the scanning unit 1 performs scanning to generate an image of the inside of the subject P. The image data generating unit 22 generates an image based on the result of scanning performed by the scanning unit 1. The marker creating unit 30 generates a marker provided with information at a position serving as a reference for comparison with the certain structure. The system control unit 90 displays the image and the marker on the same screen of the display 50.

Other Embodiments

The embodiment is not limited to the embodiments above.

The medical image diagnostic apparatus, for example, may determine whether to generate the marker depending on the examination. The medical image diagnostic apparatus, for example, may refer to the information set on the examination registration screen 51 in FIG. 3, thereby generating the marker when performing an obstetric examination or diagnosing the growth degree of a tumor.

The display 50 may be a touch panel. In this case, the display 50 receives a touch operation from the operator to move the position of the marker. A tablet terminal including a touch panel may be used as the display 50 or a sub monitor in the medical image diagnostic apparatus. The position of the marker on display is changed based on an instruction issued by an operator. Inclination of the marker on display is changed based on an instruction issued by an operator.

In the description of the embodiments above, the components of the apparatuses illustrated in the drawings are functionally conceptual ones and are not necessarily physically configured as illustrated in the drawings. In other words, a specific aspect of distribution and integration of the apparatuses is not limited to that illustrated in the drawings. A part or all of the apparatuses may be functionally or physically distributed and integrated in desired units depending on various loads and the status of use. All or a desired part of the processing functions performed by the apparatuses may be provided by a CPU and a computer program analyzed and executed by the CPU or provided as hardware by wired logic.

The control method described in the embodiments above may be performed by an image processing apparatus serving as a computer, such as a personal computer and a workstation, executing a control program provided in advance. The control program may be distributed via a network, such as the Internet. The control program may be recorded in a computer-readable recording medium, such as a hard disk, a flexible disk (FD), a compact disc read only memory (CD-ROM), a magneto-optical disc (MO), and a digital versatile disc (DVD), and executed by a computer reading it from the recording medium. The image processing apparatus may include a storage unit configured to store therein an image, a marker generating unit configured to generate a marker provided with information at a position serving as a reference for comparison with a certain structure and a control unit configured to display the image and the marker on a same screen of a display.

At least one of the embodiments described above can reduce the amount of work in the examination with a simple operation.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image diagnostic apparatus, comprising:
 a scanner configured to perform scanning to generate image signals of an inside of a subject, the subject being a woman that is pregnant with a fetus;
 image generating circuitry configured to generate an image of the fetus based on the image signals;
 marker generating circuitry configured to generate a marker provided with information at a plurality of positions serving as a reference for comparison with a certain structure, wherein the certain structure is a certain part of the fetus, and wherein the information at the plurality of positions includes a plurality of information items at each of the plurality of positions, each information item including numerical information indicating a different point of time; and
 control circuitry configured to display the image and the marker on a same screen of a display,
 wherein
 the marker generating circuitry is configured to generate the marker including the information items at positions limited to a position corresponding to a time of the scanning and at least one position respectively corresponding to at least one designated point of time that is different from the time of scanning, and the marker does not include any other information items corresponding to times other than the times corresponding to the limited positions,
 the control circuitry is further configured to, display a marker condition setting screen for receiving an instruction indicating the at least one designated point of time, and receive the instruction indicating the at least one designated point of time, and the marker generating circuitry is further configured to generate the marker such that at least one piece of numerical information respectively indicating the at least one designated point of time indicated by the received instruction is respectively provided at said at least one position respectively corresponding to the at least one designated point of time.

2. The medical image diagnostic apparatus according to claim 1, wherein the information item at each of the limited positions further includes at least one of a scale mark and characteristic information.

3. The medical image diagnostic apparatus according to claim 1, wherein the numerical information included in the information item at each of the limited positions indicates at least one of a number of months of pregnancy, a number of weeks of pregnancy, and a number of days of pregnancy.

4. The medical image diagnostic apparatus according to claim 1, wherein the marker includes a first information item at a first position, of the limited positions, indicating an estimated size of the certain structure at the time of the scanning performed by the scanner, and a second information item at a second position, of the limited positions, indicating the estimated size of the certain structure at the at least one designated point of time.

5. The medical image diagnostic apparatus according to claim 1, wherein the marker is provided with the information at the limited positions to determine appropriateness of the certain structure.

6. The medical image diagnostic apparatus according to claim 1, wherein the control circuitry changes a position of the marker on the display based on an instruction issued by an operator.

7. The medical image diagnostic apparatus according to claim 1, wherein the marker generating circuitry is further configured to generate an observation marker displayed in a first display area of the display and an identification marker corresponding to the observation marker and displayed in a second area of the display, and the control circuitry is further configured to display the identification marker in the second display area and display, upon detecting that the identification marker is selected, the observation marker in the first display area.

8. The medical image diagnostic apparatus according to claim 1, wherein the control circuitry is further configured to change an inclination of the marker on display in accordance with an instruction issued by an operator.

9. The medical image diagnostic apparatus according to claim 1, wherein the control circuitry is further configured to display, upon detecting that the image generating circuitry generates a new image, the new image on the display as a substitute for an old image previously displayed on the display, without changing display of the marker.

10. The medical image diagnostic apparatus according to claim 1, wherein the control circuitry is further configured to display the marker before displaying the image on the display.

11. The medical image diagnostic apparatus according to claim 1, wherein the marker generating circuitry is further configured to determine the limited positions at which the information is provided based on an index value statistically calculated from clinical data on the certain structure.

12. The medical image diagnostic apparatus according to claim 1, wherein the marker generating circuitry is further configured to determine the limited positions at which the information is provided based on an imaging condition to perform the scanning, and the imaging condition is a visual field depth in transmission and reception directions of ultrasonic waves.

13. The medical image diagnostic apparatus according to claim 1, wherein the marker is represented by a square.

14. The medical image diagnostic apparatus according to claim 1, wherein the marker is represented by a simple closed curve.

15. The medical image diagnostic apparatus according to claim 1, wherein the control circuitry is further configured to display the marker in response to an operation of setting examination information.

16. The medical image diagnostic apparatus according to claim 1, wherein the scanner includes an ultrasonic probe configured to transmit ultrasonic waves to the subject and receive reflected waves from the subject.

17. The medical image diagnostic apparatus according to claim 1, wherein the scanner includes a magnetostatic magnet that generates a static magnet field in an internal space, a gradient coil that generates a gradient magnetic field, a transmission coil that is arranged on an inner side of the gradient coil and generates a high-frequency magnetic field, and a reception coil that is arranged on an inner side of the gradient coil and receives a magnetic resonance signal output from the subject by an effect of the high-frequency magnetic field.

18. The medical image diagnostic apparatus according to claim 1, wherein the scanner includes an X-ray tube that irradiates the subject with X-rays and an X-ray detector that detects X-rays passing through the subject.

19. A medical image processing apparatus, comprising:

storage circuitry configured to store therein an image of a fetus in a pregnant woman;

marker generating circuitry configured to generate a marker provided with information at a plurality of positions serving as a reference for comparison with a certain part of the fetus, wherein the information includes an information item at each of the plurality of positions, the information item including numerical information indicating a different point of time; and control circuitry configured to display the image and the marker on a same screen of a display, wherein the marker generating circuitry is configured to generate the marker including the information items at positions limited to a position corresponding to a time of a scanning and at least one designated point of time that is different from the time of the scanning, and the marker does not include any other information items corresponding to times other than the times corresponding to the limited positions, the control circuitry is further configured to:

display a marker condition setting screen for receiving an instruction indicating the at least one designated point of time, and receive the instruction indicating the at least one designated point of time, and the marker generating circuitry is further configured to generate the marker such that at least one piece of numerical information respectively indicating the at least one designated point of time indicated by the received instruction is respectively provided at said at least one position respectively corresponding to the at least one designated point of time.

\* \* \* \* \*